United States Patent
Dearden et al.

(10) Patent No.: US 11,123,145 B2
(45) Date of Patent: Sep. 21, 2021

(54) COMPLIANT MECHANISMS HAVING INVERTED TOOL MEMBERS

(71) Applicant: Intuitive Surgical Operations, Inc., Sunnyvale, CA (US)

(72) Inventors: Jason Dearden, Provo, UT (US); Jordan Tanner, Cypress, TX (US); Clayton Grames, East Palo Alto, CA (US); Bryce Edmondson, Provo, UT (US); Brian D. Jensen, Orem, UT (US); Spencer P. Magleby, Provo, UT (US); Larry L. Howell, Orem, UT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 16/096,985

(22) PCT Filed: Apr. 18, 2017

(86) PCT No.: PCT/US2017/028043
§ 371 (c)(1),
(2) Date: Oct. 26, 2018

(87) PCT Pub. No.: WO2017/189272
PCT Pub. Date: Nov. 2, 2017

(65) Prior Publication Data
US 2019/0290375 A1 Sep. 26, 2019

Related U.S. Application Data

(60) Provisional application No. 62/364,469, filed on Jul. 20, 2016, provisional application No. 62/329,556, filed on Apr. 29, 2016.

(51) Int. Cl.
*A61B 34/30* (2016.01)
*A61B 17/29* (2006.01)
(Continued)

(52) U.S. Cl.
CPC .............. *A61B 34/71* (2016.02); *A61B 17/29* (2013.01); *A61B 34/30* (2016.02); *B25J 9/1045* (2013.01);
(Continued)

(58) Field of Classification Search
CPC .... A61B 2017/2937; A61B 2017/2917; A61B 2017/2932; A61B 2017/2939;
(Continued)

(56) References Cited

U.S. PATENT DOCUMENTS 3,140,614 A 7/1964 James et al.
3,482,466 A 12/1969 Orlich et al.
(Continued)

FOREIGN PATENT DOCUMENTS

CN 2626684 Y 7/2004
DE 19537320 A1 4/1997
(Continued)

OTHER PUBLICATIONS

Edmondson B.J., et al., "Oriceps: Origami-Inspired Forceps," ASME 2013 Conference on Smart Materials, Adaptive Structures and Intelligent Systems, Sep. 16-18, 2013, 6 pages.
(Continued)

*Primary Examiner* — Katherine H Schwiker

(57) ABSTRACT

The embodiments described herein can be used in a variety of grasping, cutting, and manipulating operations. In some embodiments, an apparatus includes a shaft, a tool member, and a flexure. The shaft has a distal end portion and a proximal end portion, and defines a longitudinal axis. The distal end portion includes a ground portion. The tool member has an engagement portion and an actuation portion. The engagement portion is disposed distally from the actuation portion, and can exert an engagement force on a target structure. The actuation portion receives an actuation
(Continued)

force. The flexure has a first end portion coupled to the ground portion of the shaft, and a second end portion coupled to the tool member. The flexure is configured to deform elastically when the actuation force is exerted on the actuation portion of the tool member such that the tool member rotates relative to the shaft.

21 Claims, 26 Drawing Sheets

(51) Int. Cl.
  *B25J 9/10*      (2006.01)
  *B25J 15/02*     (2006.01)
  *A61B 34/00*     (2016.01)
(52) U.S. Cl.
  CPC ... *B25J 15/0233* (2013.01); *A61B 2017/2902* (2013.01); *A61B 2017/2937* (2013.01); *A61B 2017/2939* (2013.01); *A61B 2034/305* (2016.02)
(58) Field of Classification Search
  CPC .... A61B 2017/2902; A61B 2017/2927; A61B 2017/2929; A61B 2034/305; A61B 17/29; A61B 17/28; A61B 17/2804; A61B 17/2812–282; A61B 2017/2816; A61B 2017/2901; A61B 2017/2903–2908; A61B 2017/2947; A61B 2017/2934; A61B 2017/2933; A61B 2017/2936; A61B 2017/2938; A61B 2017/2944; A61B 34/71; A61B 34/30; A61B 17/221; A61B 17/32; A61B 17/320092; A61B 17/3201; A61B 17/32056; A61B 2017/2212–2217; A61B 2017/320093–320098; A61B 10/06; B25J 15/0233; B25J 9/1045
  See application file for complete search history.

(56) References Cited

U.S. PATENT DOCUMENTS

| | | | |
|---|---|---|---|
| 4,165,745 A | 8/1979 | Heifetz | |
| 4,540,211 A | 9/1985 | Masserang | |
| 5,318,589 A | 6/1994 | Lichtman | |
| 5,496,317 A | 3/1996 | Goble et al. | |
| 5,575,805 A * | 11/1996 | Li | A61B 17/29 606/174 |
| 5,899,914 A * | 5/1999 | Zirps | A61B 17/1608 606/170 |
| 5,964,780 A | 10/1999 | Balazs | |
| 6,215,081 B1 | 4/2001 | Jensen et al. | |
| 6,322,312 B1 | 11/2001 | Sundar | |
| 6,368,290 B1 | 4/2002 | Baska | |
| 6,491,626 B1 | 12/2002 | Stone et al. | |
| 7,320,700 B2 | 1/2008 | Cooper et al. | |
| 8,245,595 B2 | 8/2012 | Milenkovic et al. | |
| 8,308,801 B2 | 11/2012 | Halverson et al. | |
| 8,323,297 B2 | 12/2012 | Hinman et al. | |
| 8,597,280 B2 | 12/2013 | Cooper et al. | |
| 8,708,593 B2 | 4/2014 | Stratton et al. | |
| 8,911,471 B2 | 12/2014 | Spivey et al. | |
| 8,945,174 B2 | 2/2015 | Blumenkranz et al. | |
| 2001/0041893 A1* | 11/2001 | Bartel | A61B 17/29 606/51 |
| 2002/0111621 A1 | 8/2002 | Wallace et al. | |
| 2005/0119527 A1 | 6/2005 | Banik et al. | |
| 2006/0184198 A1 | 8/2006 | Bales et al. | |
| 2007/0208375 A1* | 9/2007 | Nishizawa | A61B 34/71 606/205 |
| 2009/0198272 A1 | 8/2009 | Kerver et al. | |
| 2009/0209960 A1 | 8/2009 | Chojin | |
| 2010/0160735 A1 | 6/2010 | Bakos et al. | |
| 2010/0160940 A1 | 6/2010 | Lutze et al. | |
| 2011/0152879 A1 | 6/2011 | Williams et al. | |
| 2011/0276085 A1 | 11/2011 | Krzyzanowski et al. | |
| 2011/0301599 A1 | 12/2011 | Roy et al. | |
| 2013/0046317 A1 | 2/2013 | Blumenkranz | |
| 2015/0157355 A1 | 6/2015 | Price et al. | |
| 2016/0000423 A1 | 1/2016 | Shields et al. | |
| 2016/0015428 A1 | 1/2016 | Bowden et al. | |
| 2016/0022365 A1 | 1/2016 | Jensen et al. | |
| 2016/0045096 A1 | 2/2016 | Kappel et al. | |
| 2016/0051274 A1 | 2/2016 | Howell et al. | |
| 2016/0123139 A1 | 5/2016 | Jamison et al. | |
| 2016/0287279 A1 | 10/2016 | Bovay et al. | |
| 2017/0042562 A1 | 2/2017 | Moody et al. | |
| 2018/0333164 A1* | 11/2018 | Arata | A61B 17/00234 |
| 2020/0008827 A1 | 1/2020 | Dearden et al. | |
| 2020/0085415 A1 | 3/2020 | Dearden et al. | |

FOREIGN PATENT DOCUMENTS

| | | | |
|---|---|---|---|
| EP | | 1151723 A2 | 11/2001 |
| WO | WO-2010078520 A2 | | 7/2010 |
| WO | WO-2015057990 A1 | | 4/2015 |
| WO | WO-2016123139 A2 | | 8/2016 |
| WO | WO-2018052939 A1 | | 3/2018 |

OTHER PUBLICATIONS

Guerinot A.E., et al., "Compliant Joint Design Principles for High Compressive Load Situations," Journal of Mechanical Design, Department of Mechanical Engineering, Brigham Young University, Jul. 2005, vol. 127 (4), pp. 774-781.
Halverson P.A., "Multi-stable Compliant Rolling-contact Elements," Brigham Young University, May 3, 2007, 61 pages.
Lassooij J., et al., "A Statically Balanced and Bi-stable Compliant End Effector Combined with a Laparoscopic 2DoF Robotic Arm," Journal of Mechanical Sciences, 2012, vol. 3, pp. 85-93.
International Search Report and Written Opinion for Application No. PCT/US2017/028043, dated Jul. 25, 2017, 10 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Choi D.Y., et al., "Flexure-Based Manipulator for Active Handheld Microsurgical Instrument," Proceedings of the IEEE 27th Annual Conference on Engineering in Medicine and Biology, Sep. 2005, pp. 5085-5088.
Doria M., et al., "Design of an Underactuated Compliant Gripper for Surgery Using Nitinol," Journal of Medical Devices, Mar. 2009, vol. 3 (1), Abstract, p. 011007, ASME.
Extended European Search Report for Application No. EP17790117 dated Oct. 31, 2019, 8 pages.
Kota S. et al., "Design and Application of Compliant Mechanisms for Surgical Tools," Technical Briefs, Journal of Biomechanical Engineering, Nov. 2005, vol. 127, pp. 981-989, ASME.
Mertmann M., et al., "Grippers for the Micro Assembly Containing Shape Memory Actuators and Sensors," Le Journal de Physique IV France 7 (1997), Conference C5, Supplement of Journal de Physique III of Nov. 1997, pp. C5-621-C5-626.
Ramu G., et al., "A Flexure-based Deployable Stereo Vision Mechanism and Temperature and Force Sensors for Laparoscopic Tools," 14th National Conference on Machines and Mechanisms (NaCoMM09), Dec. 17-18, 2009, NaCoMM-2009-BMGR2, pp. 440-445.
Sahai R., et al., "Semi-Automated Micro Assembly for Rapid Prototyping of a One DOF Surgical Wrist," International Conference on Intelligent Robots and Systems (IROS 2003), Oct. 27-31, 2003, vol. 2, pp. 1882-1888, IEEE.
Zubir M.N.M., et al., "Development of a novel flexure based microgripper for precision manipulation of micro-objects," IEEE International Conference on Industrial Technology (ICIT 2009), 2009, pp. 1-6.

* cited by examiner

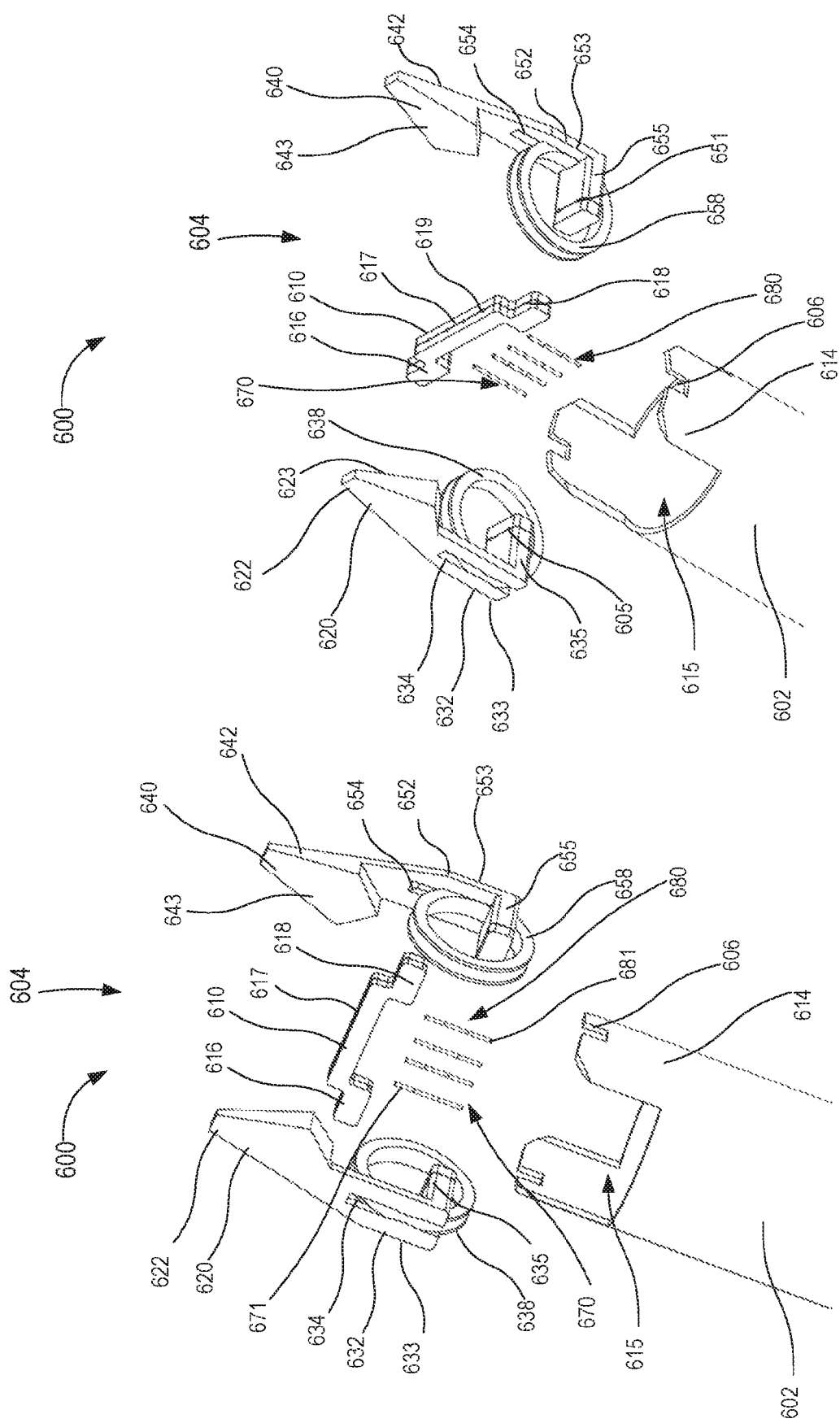

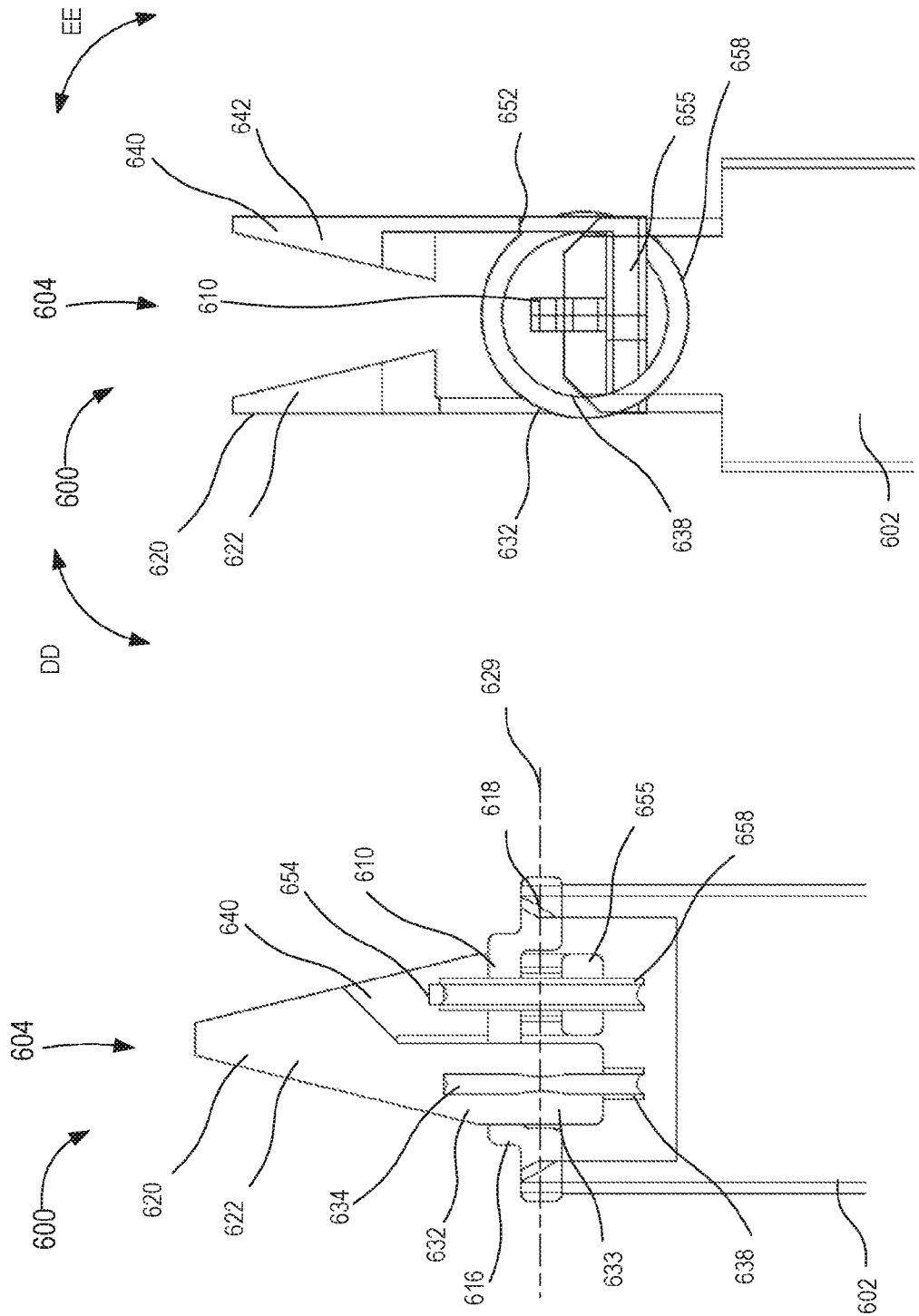

COMPLIANT MECHANISMS HAVING INVERTED TOOL MEMBERS

CROSS-REFERENCE TO RELATED APPLICATIONS

This application is a U.S. national stage filing under 35 U.S.C. § 371 of International Application No. PCT/US17/28043 (filed Apr. 18, 2017), entitled "COMPLIANT MECHANISMS HAVING INVERTED TOOL MEMBERS," which claims benefit of priority to U.S. Provisional Application No. 62/364,469 (filed Jul. 20, 2016), entitled "COMPLIANT MECHANISMS HAVING INVERTED TOOL MEMBERS," and U.S. Provisional Application No. 62/329,556 (filed Apr. 29, 2016), entitled "INVERTED GRIPPING ARM FOR A COMPLIANT MECHANISM," all of which are incorporated herein by reference in their entirety for all purposes.

BACKGROUND

The embodiments described herein relate to compliant joint mechanisms. More particularly, the embodiments described herein relate to devices having an inverted tool member (or gripping arm) for use in surgical applications.

Minimally Invasive Surgery (MIS) is a growing field, and known techniques employ tools to manipulate tissue that are both manually controlled or robotically controlled. Such known tools and mechanisms include, for example, kinematic chains including wrist mechanisms, steerable segments, grippers, cutting tools, or the like. Known methods include accessing a target work site inside a patient by at least partially following a natural lumen, such as the digestive tract, blood-carrying lumens, bronchi, or other lumens, of the patient. Following a natural lumen, for example, can allow a surgeon to operate at a work site while making fewer and/or smaller incisions through healthy tissue, although an incision may be needed at locations where the surgical device enters or leaves a natural lumen. In other MIS aspects, a surgical site is accessed without following a body lumen. Access may be via one or more incisions through the patient's body wall or via a natural orifice.

Surgeons and engineers are making continual efforts to mitigate the negative effects of surgery on patients. Reducing the size and/or the operating footprint of the surgical instruments is one method pursued in this effort. For example, when the instruments approach approximately 3 mm in diameter, they also approach a threshold where the entry incisions can be small enough so that little or no visible scar is left on the patient. But, some known tools having a diameter less than 3 mm lack the desired flexibility and may include mechanisms that produce an undesirably large swept volume inside the patient (e.g., operating footprint). For example, some known tools may lack wrist articulation and typically have one mechanical Degree of Freedom (DoF), such as grip performed by jaws. Other known tools have both wrist articulation and gripping function, but are characterized by a relatively large throw distance from the tool shaft axis to the end effector tip to accommodate the wrist articulation. Such tool designs, therefore, require more volume at a surgical site for effective tissue manipulation.

Some known instruments employ joint assemblies (e.g., for grippers) that include a pin-in-slot joint to allow one portion of the tool (e.g., a gripper) to rotate relative to a second part of the tool (e.g., a base). Such known joint mechanisms are referred to as "non-compliant" revolute joints. Such known joints can be subject to undesirable levels of friction, wear, and undesirable motion, all of which leads to a decline in performance.

Other known instruments employ joint assemblies that include a flexible member that deforms in response to an input force to produce mobility within the joint. Such joint mechanisms are referred to as "compliant joints" or "compliant mechanisms." The use of compliant mechanisms can reduce the friction, wear, and the number of parts in the joint. Some known compliant mechanisms, however, lack stability and can be susceptible to undesirable buckling during use.

Thus, a need exists for improved joint mechanisms for surgical instruments and methods of assembly and use of improved joint mechanisms.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter. In some embodiments, an apparatus includes a shaft, a tool member, and a flexure. The shaft has a distal end portion and a proximal end portion, and defines a longitudinal axis therebetween. The distal end portion of the shaft includes a ground portion. The tool member has an engagement portion and an actuation portion. The engagement portion is disposed distally from the actuation portion, and can exert an engagement force on a target structure. The actuation portion receives an actuation force. The flexure has a first end portion and a second end portion. The first end portion is coupled to the ground portion of the shaft, and the second end portion is coupled to the tool member. The flexure is configured to deform elastically when the actuation force is exerted on the actuation portion of the tool member such that the tool member rotates relative to the shaft.

In some embodiments, an apparatus includes a shaft, a tool member, and a flexure. The shaft has a distal end portion and a proximal end portion, and defines a longitudinal axis therebetween. The distal end portion of the shaft includes a ground portion. The tool member has an engagement portion and an actuation portion. The engagement portion is configured to exert an engagement force on a target structure, and the actuation portion is configured to receive an actuation force at an attachment point. The flexure is coupled to the ground portion of the shaft and the tool member. The flexure is configured to deform elastically when the actuation force is exerted on the actuation portion of the tool member such that the tool member rotates relative to the shaft about a pivot axis. The actuation portion is configured such that the attachment point is spaced apart from the pivot axis in a direction normal to the longitudinal axis by a moment distance. The moment distance varies by less than about ten percent through an angular range of motion of the tool member.

BRIEF DESCRIPTION OF THE DRAWINGS

FIGS. 22 and 23 are perspective exploded views of the surgical assembly shown in FIGS. 20 and 21.

FIG. 24 is a side view of the surgical assembly shown in FIGS. 20 and 21.

FIG. 25 is a front view of the surgical assembly shown in FIGS. 20 and 21, in a first configuration.

DETAILED DESCRIPTION

Figure 2:
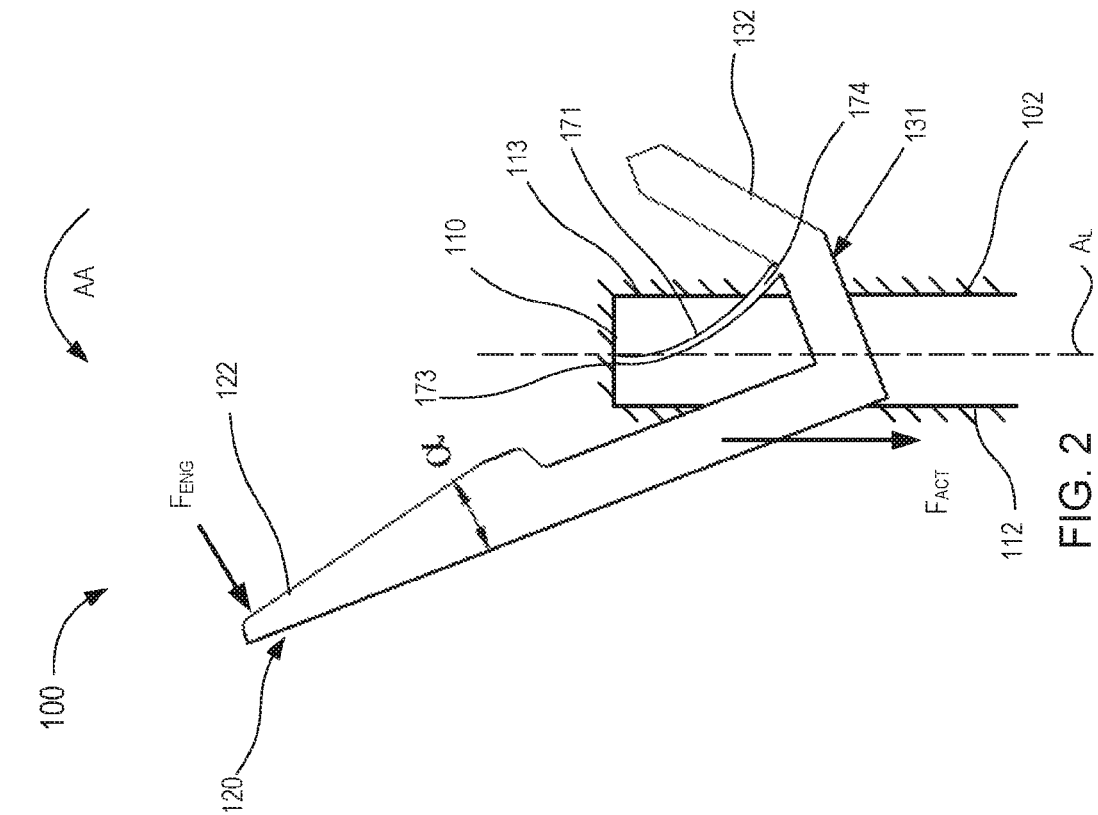
FIGS. 1 and 2 are schematic illustrations of a compliant joint mechanism according to an embodiment, in a first configuration and a second configuration, respectively.

The embodiments described herein can advantageously be used in a wide variety of grasping, cutting, and manipulating operations. In particular, the inverted flexure designs described herein can allow a single compliant segment (or compliant segment assembly) to deflect to produce both gripping motion and wrist motion of an end effector tool with respect to a mounting shaft. As described herein, the flexures are inverted so that the loads on the flexure are in tension and bending rather than in compression, thus avoiding buckling. The embodiments described herein include joints having an end effector tool (e.g., shears or grasper) with two degrees of freedom that minimizes or reduces friction. The embodiments described herein have mechanisms providing relatively low friction. The embodiments described herein include at least a two-degree-of-freedom tool at small scales, and that has a minimum or reduced number of parts. In other embodiments, however, a tool, a joint assembly, or both, has only one degree-of-freedom.

In some embodiments, an apparatus includes a shaft, a tool member, and a flexure. The shaft has a distal end portion and a proximal end portion, and defines a longitudinal axis therebetween. The distal end portion of the shaft includes a ground portion. The tool member has an engagement portion and an actuation portion. The engagement portion is disposed distally from the actuation portion, and can exert an engagement force on a target structure. The actuation portion receives an actuation force. The flexure has a first end portion and a second end portion. The first end portion is coupled to the ground portion of the shaft, and the second end portion is coupled to the tool member. The flexure is configured to deform elastically when the actuation force is exerted on the actuation portion of the tool member such that the tool member rotates relative to the shaft.

In some embodiments, an apparatus includes a shaft, a tool member, and a flexure. The shaft has a distal end portion and a proximal end portion, and defines a longitudinal axis therebetween. The distal end portion of the shaft includes a ground portion. The tool member has an engagement portion and an actuation portion. The engagement portion is configured to exert an engagement force on a target structure, and the actuation portion is configured to receive an actuation force at an attachment point. The flexure is coupled to the ground portion of the shaft and the tool member. The flexure is configured to deform elastically when the actuation force is exerted on the actuation portion of the tool member such that the tool member rotates relative to the shaft about a pivot axis. The actuation portion is configured such that the attachment point is spaced apart from the pivot axis in a direction normal to the longitudinal axis by a moment distance. The moment distance varies by less than about ten percent through an angular range of motion of the tool member.

In some embodiments, an apparatus includes a shaft, a first tool member, a second tool member and a flexure assembly. The shaft has a distal end portion and a proximal end portion, and defines a longitudinal axis therebetween. The distal end portion of the shaft includes a ground portion. The first tool member has a first engagement portion and a first actuation portion, the first actuation portion being configured to receive a first actuation force. The second tool member has a second engagement portion and a second actuation portion, the second actuation portion being configured to receive a second actuation force. The flexure assembly is coupled to the ground portion of the shaft and is disposed between a proximal-most surface of the first actuation portion and the first engagement portion, the first tool member, and the second tool member. A first portion of the flexure assembly is configured to deform elastically when the first actuation force is exerted on the first actuation portion of the tool member such that the first tool member rotates relative to the shaft. A second portion of the flexure assembly is configured to deform elastically when the second actuation force is exerted on the second actuation portion of the tool member such that the second tool member rotates relative to the shaft.

Methods of using a joint assembly are also described herein. In some embodiments, a method includes moving a shaft of a medical device such that an engagement portion of a tool member is placed in a delivery position relative to a target structure. The shaft defines a longitudinal axis. The tool member is coupled to a ground portion of the shaft via a flexure that is disposed between the engagement portion and a proximal-most surface of an actuation portion of the tool member. An actuation force is exerted on the actuation portion, and causes the flexure to deform elastically such that the tool member rotates relative to the shaft. The engagement portion of the tool member exerts an engagement force on the target structure when the tool member is rotated.

As used herein, the term "about" when used in connection with a referenced numeric indication means the referenced numeric indication plus or minus up to 10% of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g. a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein. A flexible part may have infinite degrees of freedom (DOF's).

Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links.

As used in this specification and the appended claims, the words "proximal" and "distal" refer to direction closer to and away from, respectively, an operator (or controller) of the surgical device. Thus, for example, the end of a joint assembly that is farthest away from the user (and that is closest to the target tissue) would be the distal end of the joint assembly, while the end opposite the distal end (i.e., the end manipulated by the user or coupled to the actuation shaft) would be the proximal end of the joint assembly.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, joint mechanism, joint assembly, and variants thereof, can be interchangeably used.

Aspects of the invention are described primarily in terms of an implementation using a surgical system, such as, for example, the da Vinci® Surgical System, commercialized by Intuitive Surgical, Inc. of Sunnyvale, Calif. Examples of such surgical systems are the da Vinci® Xi™ Surgical System (Model IS4000) and the da Vinci® Si™ HD™ Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200), or any other surgical assemblies, are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

Figure 1:
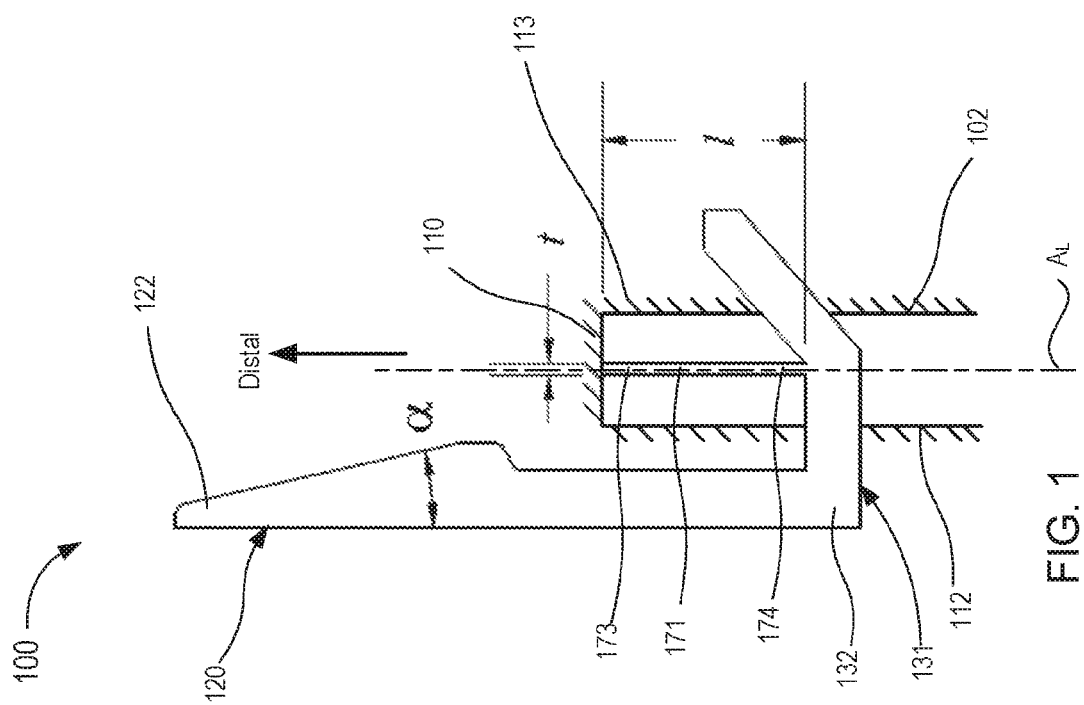

FIGS. 1 and 2 are schematic illustrations of a compliant joint assembly 100, according to an embodiment. The joint assembly 100 includes a shaft 102, a tool member 120, and a flexure 171. The joint assembly 100, and any of the joint assemblies described herein, can be used in any suitable surgical device or system as described herein. For example, the tool member 120 and the flexure 171 are optionally parts of an end effector, such as a gripper, shears, or the like. The shaft 102 can be coupled to the distal end of a surgical instrument shaft, either directly or via a wrist assembly that allows the end effector to change orientation (e.g., one or more of roll, pitch, and yaw) with reference to the shaft.

The shaft 102 has a proximal end portion 112 and a distal end portion 113. The shaft 102 defines a longitudinal axis $A_L$, along which the distal and proximal directions are defined (see, e.g., the arrow indicating the distal direction). The distal end portion 113 of the shaft 102 includes a ground portion 110. The ground portion 110 is a part of, or fixedly coupled to, the shaft 102, and serves as a point of attachment for the tool member 120 (via the flexure 171).

The tool member 120 includes an engagement portion 122 and an actuation portion 132. As shown in FIG. 2, the engagement portion 122 is disposed distally from the actuation portion 132, and is configured to exert an engagement force FENG on a target structure (not shown). The engagement portion 122 can include an engagement surface that forms an angle α. The engagement angle α is defined between the engagement surface and the longitudinal axis $A_L$ when the tool member 120 is in the resting (or undeflected) configuration. As described in more detail herein, in some embodiments, the angle α of the engagement surface can be selected so that the engagement surface remains flush with another structure (e.g., a second tool member, a fixed surface, a target structure or the like) throughout the range of angular motion of the tool member 120. In some embodiments, for example, the tool member 120 can move relative to a fixed portion of a jaw (not shown) that is coupled to the shaft 102. In other embodiments, the compliant joint assembly 100 can include multiple moving tool members (not shown) that cooperatively perform gripping or shearing functions.

The target structure can be internal or external tissue within a patient that is manipulated by the tool member. For example, a target tissue can be cancer cells, tumor cells, lesions, vascular occlusions, thrombosis, calculi, uterine fibroids, bone metastases, adenomyosis, or any other bodily tissue. Furthermore, the presented examples of target structures are not an exhaustive list. Moreover, a target structure can also include an artificial substance (or non-tissue) within or associated with a body, such as for example, a stent, a portion of an artificial tube, a fastener within the body or the like. The engagement portion 122 can be, for example, a gripping portion, a shear, or the like.

The actuation portion 132 is configured to receive an actuation force FACT to actuate the tool member 120, as shown in FIG. 2. The actuation force FACT can be exerted on the actuation portion 132 in any suitable manner and at any location. For example, although the actuation portion 132 is shown as receiving the actuation force FACT at a single point, in other embodiments, the actuation portion 132 can include multiple points of contact upon which an actuation force can be exerted. In some embodiments, the actuation force FACT can be exerted on the actuation portion 132 via a flexible cable, a rigid linkage (e.g., a push/pull rod) or any other suitable force-transmitting member (not shown in FIGS. 1 and 2).

The tool member 120 is coupled to the ground portion 110 of the shaft 102 via the flexure 171. More specifically, the flexure 171 has a first end portion 173 and a second end portion 174. The first end portion 173 is coupled to the ground portion 110 of the shaft 102, and the second end portion 174 is coupled to the tool member 120. As shown in FIG. 2, the flexure 171 is configured to deform elastically when the actuation force FACT is exerted on the actuation portion 132 of the tool member 120 such that the tool member 120 rotates relative to the shaft 102, as shown by the arrow AA. Thus, the flexure 171 is a resilient member that stores energy from the actuation force FACT and releases the energy when the actuation force FACT is removed, thus allowing the tool member to repeatedly rotate relative to the shaft 102. This arrangement results in a mechanism with low part count, reduced friction, and the ability to scale the device to smaller sizes, as compared to a traditional pin joint.

The flexure 171 and any of the flexures described herein can have any suitable shape and can be constructed from any suitable material to produce the desired flexibility, resilience, and durability during operation. For example, in some embodiments, the flexure 171 (and any of the flexures shown herein) can be a small rod-shaped member having a circular cross-sectional shape. In other embodiments, the flexure 171 (and any of the flexures shown herein) can be a thin, flat member having a rectangular cross-sectional shape. Moreover, in some embodiments, the flexure 171 (and any of the flexures shown herein) can be constructed from stainless steel, titanium, metallic glass, and the nickel titanium alloy Nitinol. Nitinol (also referred to as NiTi) includes nearly equal atomic percentages of nickel and titanium. NiTi can exhibit the superelastic effect and is therefore suitable for use in the compliant mechanisms described herein due to the large strains that it can undergo before yielding. Flexures constructed from NiTi can reach strains of between about 6% and about 8% with very small material set. Conversely, steels generally reach strains on the order of less than 1% before yielding.

As shown in FIGS. 1 and 2, the tool member 120 is coupled to shaft 102 in a manner that produces an inverted configuration. Similarly stated, the tool member 120 is coupled to the shaft 102 in a manner such that the flexure 171 is placed in tension when the actuation force FACT is exerted on the actuation portion 132 of the tool member 120 during normal use. This arrangement eliminates the likelihood that the flexure 171 will be exposed to a buckling load, thereby improving the performance of the compliant mechanism. In some embodiments the inverted configuration is achieved by having the flexure 171 disposed between the engagement portion 122 and a proximal-most surface 131 of the actuation portion 132, as shown in FIGS. 1 and 2. In other embodiments, the tool member 120 is coupled to the shaft 102 such that the ground portion 110 of the shaft 102 is disposed between the engagement portion 122 and the proximal-most surface 131 of the actuation portion 132. In yet other embodiments, the engagement portion 122 of the tool member 120 includes an engagement surface disposed distally from each of the actuation portion 132, the ground portion 110, and the flexure 171.

Thus, the tool member 120, flexure 171 and ground portion 110 are arranged to accommodate application of a tensile actuation force $F_{ACT}$. Although the actuation force FACT is shown as being parallel to the longitudinal axis $A_L$ and being solely in the proximal direction, in other embodiments, only a component of the actuation force FACT has a proximal direction. Said another way, the actuation force $F_{ACT}$ (and any of the actuation forces described herein) can form a non-zero angle with the longitudinal axis $A_L$.

Figure 4:
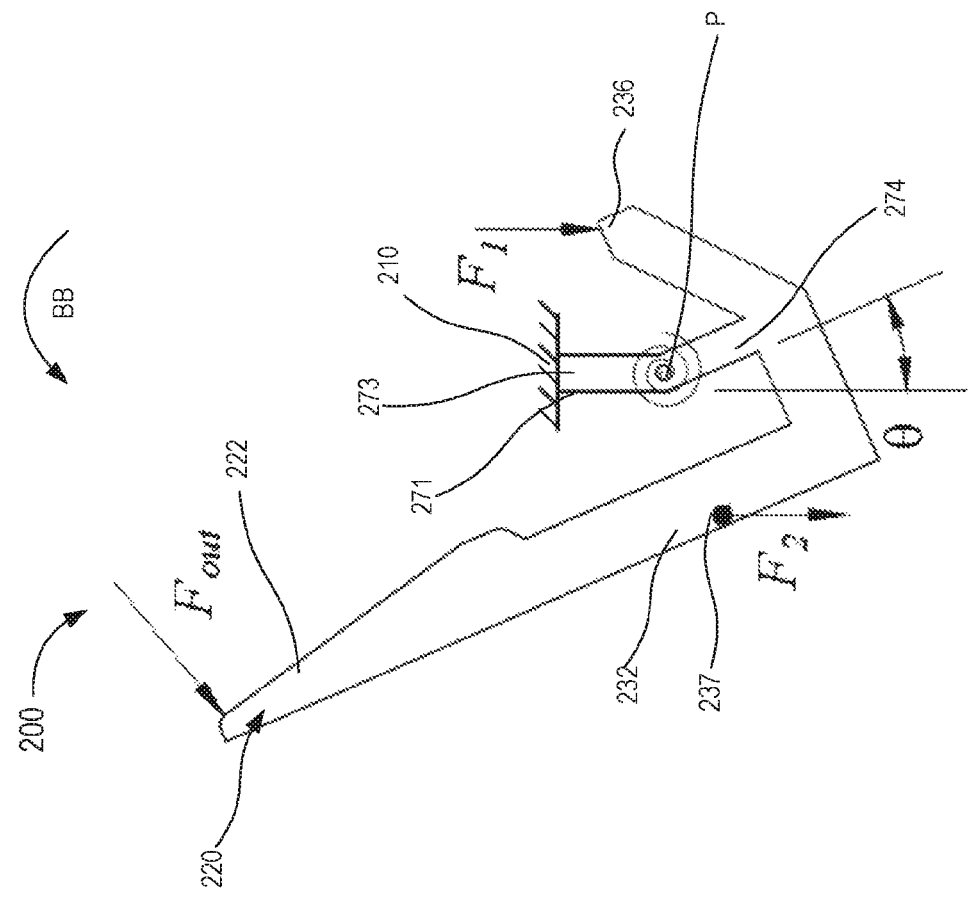
FIGS. 3 and 4 are schematic illustrations of a compliant joint mechanism according to an embodiment, represented as a pseudo-rigid-body model in a first configuration and a second configuration, respectively.
Figure 3:
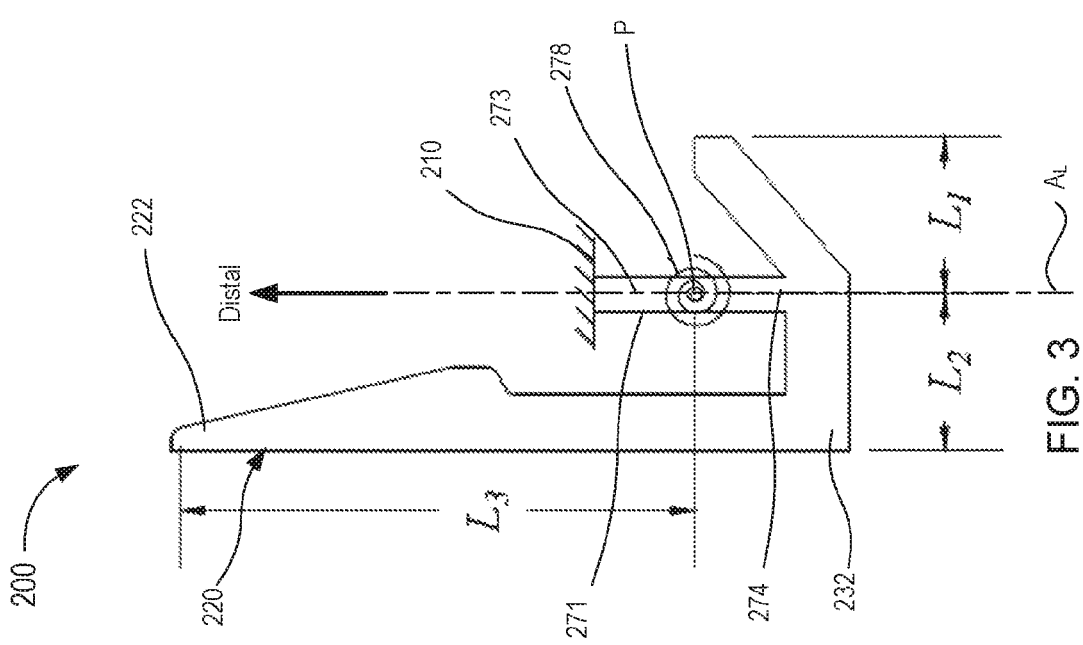

As shown in FIG. 2, during use the flexure 171 deforms to allow angular rotation of the tool member 120 relative to the shaft 102. The range of motion of the flexure 171, and therefore the tool member 120 can be modeled using a pseudo-rigid-body model. This is shown in FIGS. 3 and 4, which are schematic illustrations of a compliant joint mechanism 200 according to an embodiment, that is represented as a pseudo-rigid-body model. The joint mechanism 200 is shown in a first configuration (FIG. 3) and a second configuration (FIG. 4). The joint mechanism 200 includes a shaft (not shown) having a ground portion 210, a tool member 220, and a flexure 271. The joint assembly 200, and any of the joint assemblies described herein, can be used in any suitable surgical device or system as described herein.

The shaft defines a longitudinal axis $A_L$, along which the distal and proximal directions are defined (see, e.g., the arrow indicating the distal direction). The ground portion 210 is a part of, or fixedly coupled to, the shaft, and serves as a point of attachment for the tool member 220 (via the flexure 271). The tool member 220 can be similar to the tool member 120 described above, and includes an engagement portion 222 and an actuation portion 232. As shown in FIG. 4, the engagement portion 222 is disposed distally from the actuation portion 232, and is configured to exert an engagement force $F_{OUT}$ on a target structure (not shown). The engagement portion 222 can be, for example, a gripping portion, a shear, or the like.

The actuation portion 232 is configured to receive the actuation forces $F_1$ and $F_2$ to actuate the tool member 220, as shown in FIG. 4. The actuation forces $F_1$ and $F_2$ can be exerted on the actuation portion 232 in any suitable manner and at any location. For example, as shown in FIG. 4, the actuation portion 232 includes a first connection point 236 at which the first actuation force $F_1$ is exerted. The actuation portion 232 includes a second connection point 237 at which the second actuation force $F_2$ is exerted. The actuation forces $F_1$ and $F_2$ can be exerted on the actuation portion 232 via a flexible cable, a rigid linkage (e.g., a push/pull rod) or any other suitable force-transmitting member (not shown in FIGS. 3 and 4).

The tool member 220 is coupled to the ground portion 210 via the flexure 271. More specifically, the flexure 271 has a first end portion 273 and a second end portion 274. The first end portion 273 is coupled to the ground portion 210, and the second end portion 274 is coupled to the tool member 220. In this manner, the tool member 220 is coupled to shaft in a manner that produces an inverted configuration. Similarly stated, the tool member 220 is coupled to the shaft in a manner such that the flexure 271 is placed in tension when the actuation forces $F_1$ and $F_2$ are exerted on the actuation portion 232 of the tool member 220 during normal use. As shown, the inverted configuration is achieved by having the flexure 271 disposed between the engagement portion 222 and a proximal-most surface of the actuation portion 232. Similarly, the tool member 220 is coupled to the shaft such that the ground portion 210 is disposed between the engagement portion 222 and the proximal-most surface of the actuation portion 232. In some embodiments, the engagement portion 222 of the tool member 220 includes an engagement surface disposed distally from each of the actuation portion 232, the ground portion 210, and the flexure 271.

In the pseudo-rigid-body model (PRBM), the motion can be approximated as that of a pin joint that rotates about a single point P with a torsional spring 278. The pivot point P is referred to as the characteristic pivot, and is located half the distance of the flexure length from its fixed point (at the ground 210). As shown in FIG. 3, when the tool member 220 is in the undeflected position, the actuation forces $F_1$ and $F_2$ are exerted at the same position along the longitudinal axis $A_L$ as the characteristic pivot P. This arrangement minimizes the amount of cable stretch or cable slack in those embodiments in which the cable is attached to the same actuating spool (see, e.g., FIG. 17). In other embodiments, however, either the first connection point 236 or the second connection point 237 (or both) can be at any suitable position along the longitudinal axis $A_L$. For example, in some embodiments, either the first connection point 236 or the second connection point 237 (or both) can be located distally from the characteristic pivot point P. In other embodiments, either the first connection point 236 or the second connection point 237 (or both) can be located proximally from the characteristic pivot point P.

As shown in FIG. 4, the flexure 271 is configured to deform elastically when the actuation forces $F_1$ and $F_2$ are exerted on the actuation portion 232 of the tool member 220 such that the tool member 220 rotates relative to the shaft 202, as shown by the arrow BB. This is modeled using the PRBM as the second end portion 274 of the flexure 271 rotating about the characteristic pivot P by an angle of θ.

Figure 5:
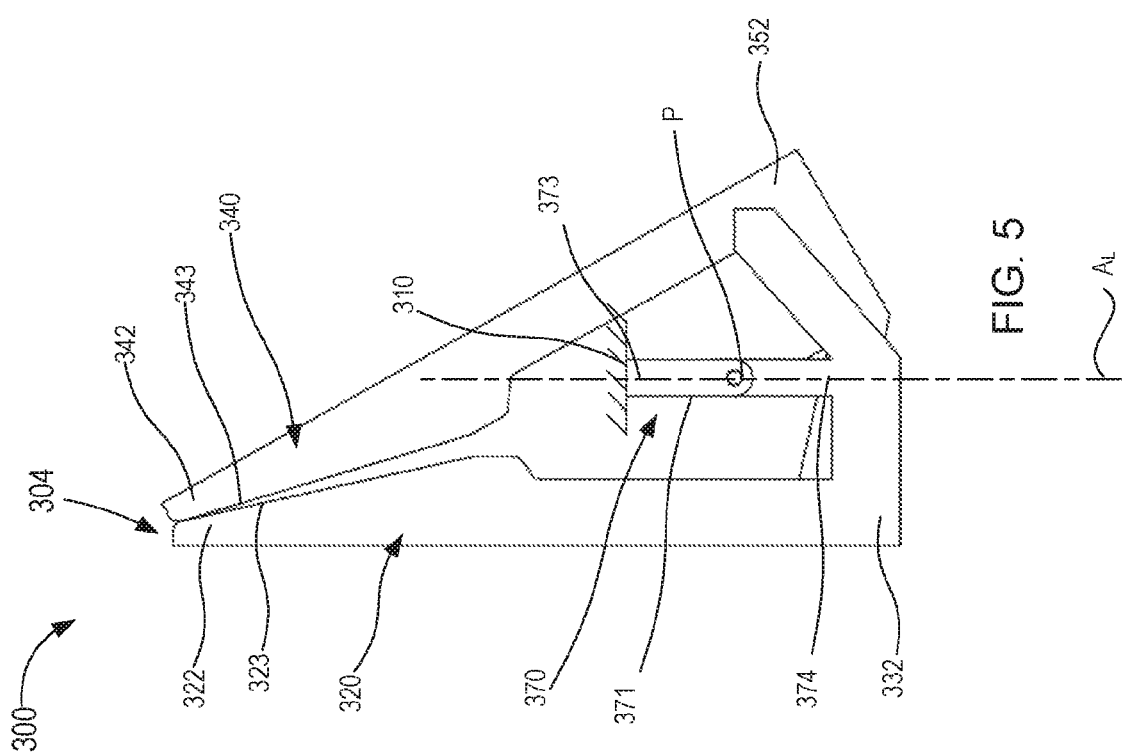
FIG. 5 is a schematic illustration of an end effector having two inverted tool members, according to an embodiment.

Although the joint assemblies 100 and 200 are shown as including only a single tool member, in other embodiments, a joint assembly can include any number of tool members. For example, FIG. 5 is a schematic illustration of a joint mechanism 300 (also called "joint assembly 300") according to an embodiment. The joint mechanism 300 may be comprise a compliant mechanism. The joint mechanism 300 includes a shaft (not shown) having a ground portion 310, a first tool member 320, a second tool member 340, and a flexure assembly 370. The first tool member 320 and the second tool member 340 can be a portion of an end effector 304 for a surgical instrument. The joint mechanism 300, and any of the joint assemblies described herein, can be used in any suitable surgical device or system as described herein.

Figure 8:
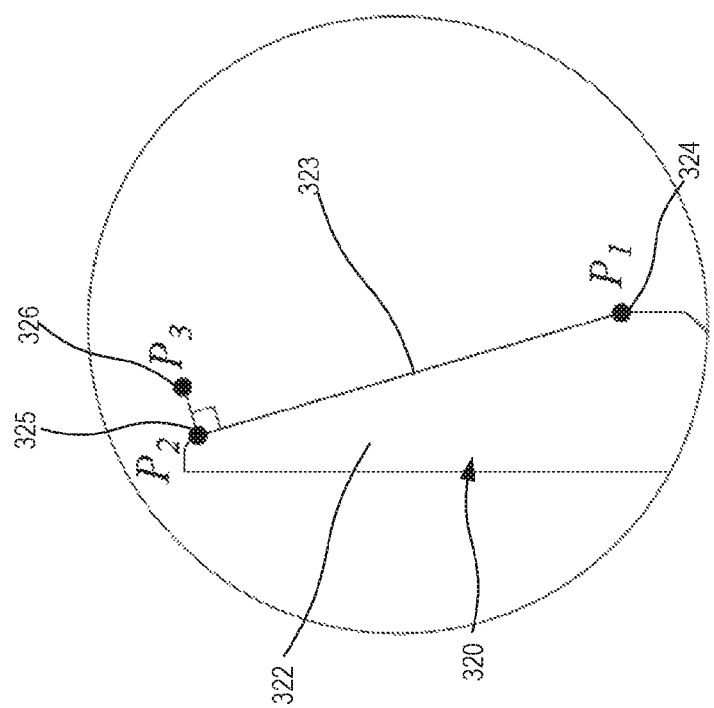
FIG. 8 is a close-up view of a portion of the tool member shown in FIG. 7.
Figure 7:
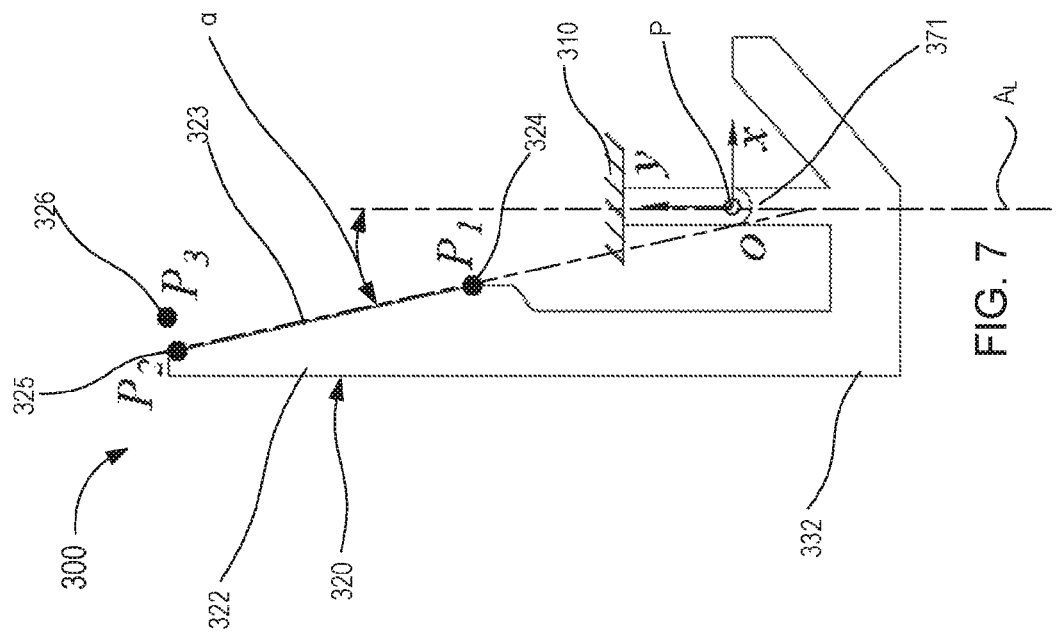

The shaft defines a longitudinal axis $A_L$, along which the distal and proximal directions are defined. The ground portion 310 is a part of, or fixedly coupled to, the shaft, and serves as a point of attachment for the first tool member 320 and the second tool member 340 (via the flexure assembly 370). The first tool member 320 includes an engagement portion 322 and an actuation portion 332. As shown in FIG. 5, the engagement portion 322 is disposed distally from the actuation portion 332, and is configured to exert an engagement force (not shown, similar to the force $F_{OUT}$) on a target structure (not shown). Specifically, the engagement portion 322 includes an engagement surface 323. Moreover, as shown in FIGS. 7 and 8, the engagement portion 322 defines several characteristic points of contact, including the point P1 (also identified as point 324), the point P2 (also identified as point 325), and the point P3 (also identified as point 326, see FIG. 8).

The actuation portion 332 of the first tool member 320 is configured to receive the actuation forces (not shown, but similar to the forces $F_1$ and $F_2$ described above) to actuate the first tool member 320. The actuation forces can be exerted on the actuation portion 332 in any suitable manner and at any location. For example, in some embodiments, the actuation forces can be exerted at a first actuation point 336 and a second actuation point 337 (see FIG. 9). Moreover, the actuation forces can be exerted on the actuation portion 332 via a flexible cable, a rigid linkage (e.g., a push/pull rod) or any other suitable force-transmitting member (not shown in FIG. 5).

The second tool member 340 includes an engagement portion 342 and an actuation portion 352. As shown in FIG. 5, the engagement portion 342 is disposed distally from the actuation portion 352, and is configured to exert an engagement force (not shown, similar to the force $F_{OUT}$) on a target structure (not shown). Thus, the first tool member 320 and the second tool member 340 can together (or collectively) exert an engagement force on the target structure that is located between the engagement portion 322 and the engagement portion 342. Specifically, the engagement portion 342 includes an engagement surface 343. Moreover, the engagement portion 342 of the second tool member 340 can define several characteristic points of contact similar to the point P1, the point P2, and the point P3 defined for the first tool member 320. The actuation portion 352 of the second tool member 340 is configured to receive the actuation forces (not shown, but similar to the forces $F_1$ and $F_2$ described above) to actuate the second tool member 340. The actuation forces can be exerted on the actuation portion 352 in any suitable manner and at any location. Moreover, the actuation forces can be exerted on the actuation portion 352 via a flexible cable, a rigid linkage (e.g., a push/pull rod) or any other suitable force-transmitting member (not shown in FIG. 5).

The first tool member 320 and the second tool member 340 are coupled to the ground portion 310 via the flexure assembly 370. The flexure assembly 370 includes a first flexure 371 and a second flexure (not shown in FIG. 5). The first flexure 371 has a first end portion 373 and a second end portion 374. The first end portion 373 is coupled to the ground portion 310, and the second end portion 374 is coupled to the first tool member 320. In this manner, the tool member 320 is coupled to the shaft in a manner that produces an inverted configuration, as described above.

As described above with reference to the joint mechanism 200, the first flexure 371 is configured to deform elastically when the actuation forces are exerted on the actuation portion 332 of the first tool member 320 such that the first tool member 320 rotates relative to the shaft. This is modeled using the PRBM as the second end portion 374 of the first flexure 371 rotating about a characteristic pivot P.

In some embodiments, the engagement surface 323 and the engagement surface 343 are designed (or have an orientation) such that they close at upon each other throughout the entire range of motion of the joint mechanism 300. In some embodiments, the engagement surface 323 and the engagement surface 343 are each planar, and are configured to be parallel to ("flush with") each other when the first tool member 320 and the second tool member 340 close upon each other throughout the range of motion. In other embodiments, it may be desired for the tips of the engagement portions 322, 342 to meet slightly ahead of the base of the engagement portions 322, 342, as shown in FIG. 5 (with contact occurring at or near point P2). In some instances, however, it can be undesirable for the base of the engagement portions 322, 342 to meet prior to the tips of the engagement portions 322, 342 meeting. To facilitate design of the first tool member 320 and the second tool member 340 to ensure that the engagement surfaces 322, 342 contact as desired, the following kinematic analysis can be applied to the joint mechanism 300.

As discussed above, FIGS. 6 and 7 identify three key points: the origin O (which is coincident with the characteristic pivot point P), and two points on the engagement surface 323, point P1 and point P2. In some embodiments, these three points can be collinear. Said another way, in some embodiments, the engagement surface 323 defines an engagement plane that intersects the pivot axis P. Moreover, the engagement plane can intersect the pivot axis P over the entire range of angular motion of the first tool member 320. The range of motion for the first tool member 320 (and any of the tool members shown and described herein) can be within ±30 degrees, ±45 degrees, ±60 degrees, ±75 degrees, or ±90 degrees.

Based on the pseudo-rigid body model, the first tool member 320 and the second tool member 340 will each pivot about the characteristic pivot P, which is the same location as the origin O. Because the first tool member 320 and the second tool member 340 both pivot about this common point, the requirement of collinearity will ensure that the surfaces of the jaws always meet. Vectors from the origin O can be used to define points $P_1$ and $P_2$. For the undeflected position, these vectors are defined as:

$$P_1 = (-x_1)\hat{i} + (y_1)\hat{j} \qquad \text{Eq. (1)}$$

$$P_2 = P_1 + [-(x_2 - x_1)\hat{i} + (y_2 - y_1)\hat{j}] \qquad \text{Eq. (2)}$$

$$= (-x_2)\hat{i} + (y_2)\hat{j} \qquad \text{Eq. (3)}$$

With the assumption of collinearity, $P_2$ can be defined as $P_1$ multiplied by a scalar, c, as in:

$$P_2 = cP_1 \qquad \text{Eq. (4)}$$

$$(-x_2)\hat{i} + (y_2)\hat{j} = c[(-x_1)\hat{i} + (y_1)\hat{j}] \qquad \text{Eq. (5)}$$

Decomposing Eq. 5 into its I and J components yields the following constraints:

$$-x_2 = -cx_1 \qquad \text{Eq. (6)}$$

$$y_2 = cy_1 \qquad \text{Eq. (7)}$$

Substituting Eq. 6 into Eq. 7 will yield an equation which, if satisfied, ensures that the engagement surface 323 and the engagement surface 343 (also referred to as the faces of the two jaws) meet flush at any given angle of motion (within the bounds that will be discussed later). This equation is given as:

$$\frac{x_1}{y_1} = \frac{x_2}{y_2} \qquad \text{Eq. (8)}$$

As discussed above, in other embodiments, it may be acceptable for the tips of the engagement portions 322, 342 to meet slightly ahead of the base of the engagement portions 322, 342, as shown in FIG. 5 (with contact occurring at or near point P2). In such embodiments, the engagement plane does not intersect the pivot axis P. In some embodiments, for example, the engagement plane can define an angle $\alpha$ (see FIG. 7) with respect to the longitudinal axis $A_L$ that is greater than about 5 degrees.

Moreover, in some embodiments, the joint mechanism 300 (and any of the joint mechanisms described herein) can be modeled to define a third point, $P_3$. The third point $P_3$ can be defined at some point near point $P_2$ but slightly offset from the engagement surface 323, as shown in FIGS. 7 and 8. Two more vectors can be used to define point $P_3$—a vector from the origin to $P_3$ and a vector from $P_2$ to $P_3$ ($P_{2,3}$). For simplicity, $P_{2,3}$ can be defined orthogonal to $P_2$ as in Eqs. 9 and 10 below. Furthermore, the offset distance, or magnitude of $P_{2,3}$, can be defined as a fraction of the length of the tool member 320 (or jaw). For example, if $d_{jaw}$ is used as a scalar, Eq. 11 can be used to determine the offset distance.

$$P_{2,3} \perp P_2 \qquad \text{Eq. (9)}$$

$$P_2 \cdot P_{2,3} = 0 \qquad \text{Eq. (10)}$$

$$\|P_{2,3}\| = d_{jaw}\|P_2 - P_1\| \qquad \text{Eq. (11)}$$

To solve for $P_{2,3}$, Eq. 10 can be expanded as shown in Eq. 12 where $x_{23}$ and $y_{23}$ represent the I and J components of $P_{2,3}$, respectively. This provides one equation, but two unknown values. The expanded form of Eq. 11 can serve as a second equation and is shown in Eq. 13.

$$[(-x_2)\hat{i}+(y_2)\hat{j}]\cdot[x_{23}\hat{i}+y_{23}\hat{j}]=0 \qquad \text{Eq. (12)}$$

$$\sqrt{(x_{23})^2+(y_{23})^2}=d_{jaw}\sqrt{(x_1-x_2)^2+(y_2-y_1)^2} \qquad \text{Eq. (13)}$$

These two equations can be solved simultaneously for $x_{23}$ and $y_{23}$ which results in the following equations:

$$x_{23} = \frac{y_2}{x_1}\left[\frac{d_{jaw}^2}{\left(\frac{y_2}{x_1}\right)^2+1}[(x_1-x_2)^2+(y_2-y_1)^2]\right]^{1/2} \qquad \text{Eq. (14)}$$

$$y_{23} = \left[\frac{d_{jaw}^2}{\left(\frac{y_2}{x_1}\right)^2+1}[(x_1-x_2)^2+(y_2-y_1)^2]\right]^{1/2} \qquad \text{Eq. (15)}$$

Once these points are calculated, the tool member (or jaw) can be designed to extend from $P_1$ to $P_3$ rather than from $P_1$ to $P_2$. The derivation of these equations is based on the assumption that the small length flexural pivots of the two tool members 320, 340 act purely as a pin joint.

Figure 6:
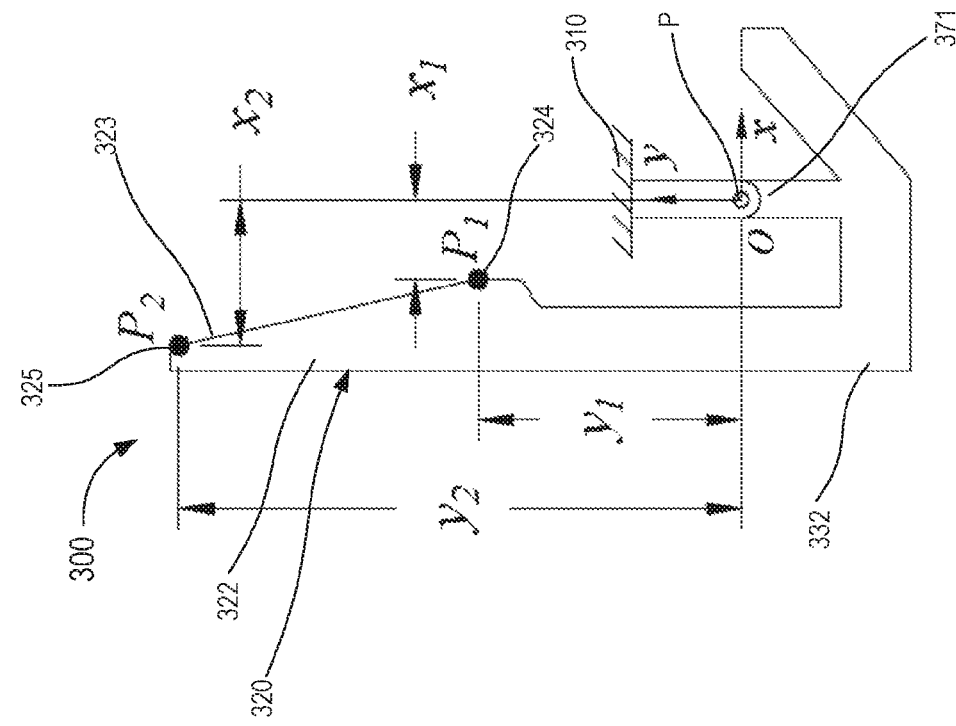
FIGS. 6 and 7 are schematic illustrations of a tool member of the end effector shown in FIG. 5.
Figure 9:
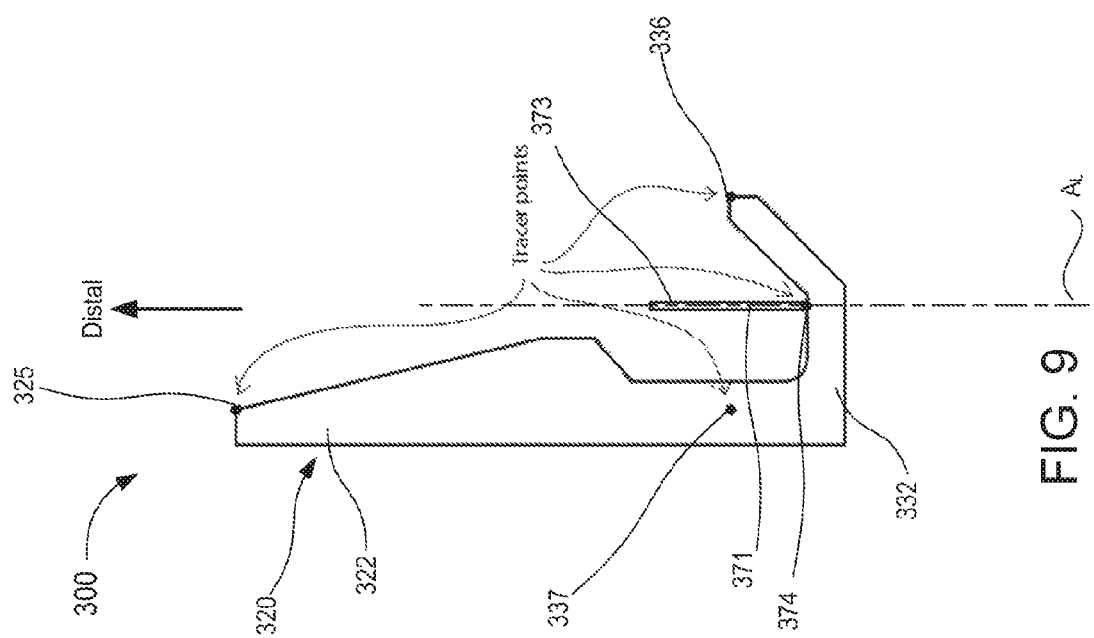
FIG. 9 is a schematic illustration of the tool member shown in FIGS. 5-7.

To assess the accuracy of the kinematic modeling, a comparison between the pseudo-rigid body model and a finite element model was performed. The comparison was based on the joint mechanism 300 shown in FIGS. 5-9. In particular, FIG. 9 shows the tool member 320 and the flexure 371, but represents the flexure 371 as a solid member, rather than using the two-piece model with the characteristic pivot point P that is shown in FIGS. 5-7. Additionally, the tool member 320 shown in FIG. 9 defines four points: one point at the bottom of the second end portion of the flexure 371, one point at each of the input force locations on the actuation portion 332 (identified as points 336 and 337), and one point at the distal-most tip of the engagement portion 322 (point P2, 325). For the purpose of modeling, the dimensions for the tool member 320 were as shown in Table 1, below.

TABLE 1

Geometric Design Boundary Conditions

| Parameter | Reference FIG. | Value |
|---|---|---|
| $L_1$ | FIG. 3 | 1.30 mm |
| $L_2$ | FIG. 3 | 1.30 mm |
| $L_3$ | FIG. 3 | 6.35 mm |
| $\alpha$ | FIGS. 1, 2, 7 | 12.5 degrees |
| l | FIG. 1 | 2.00 mm |
| w | See FIG. 1; width is normal to t and l | 0.50 mm |
| t | FIG. 1 | 0.080 mm |

Figure 10:
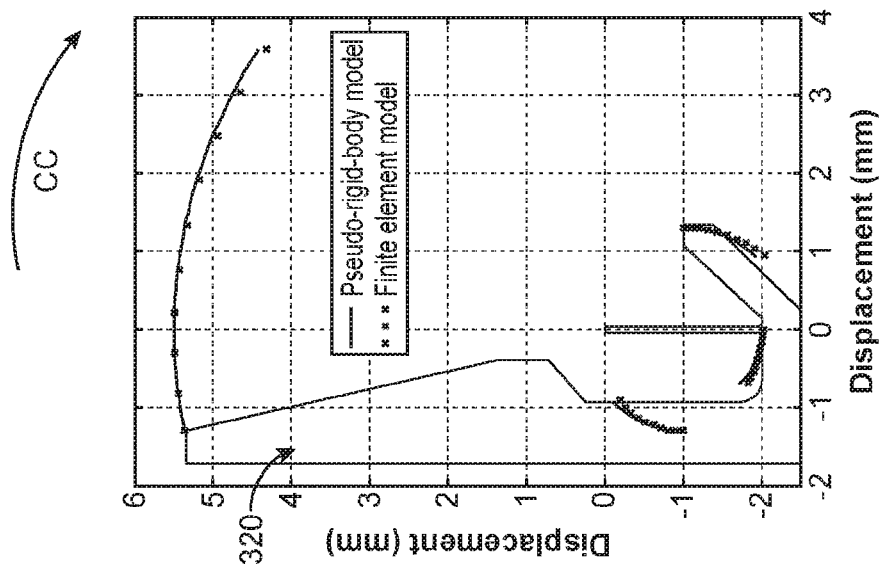
FIG. 10 is a graph showing the calculated displacement over a range of rotational motion of the tool member shown in FIG. 9.

The plot shown in FIG. 10 shows the motion paths that each selected point follows as the tool member 320 is actuated to rotate from the undeflected configuration of 0 degrees to 45 degrees (shown by the arrow CC in FIG. 10). As shown, the pseudo-rigid-body calculations and the finite element models agree closely with one another. Although the calculations and modeling above are described for the joint mechanism 300 with the boundary conditions as provided in Table 1, the general results are applicable to any of the joints shown and described herein, including all compliant joints described.

The joint mechanism 300 (and any of the other joint or compliant mechanisms described herein) can be configured to produce the desired mechanical advantage over the range of motion of the tool member. The mechanical advantage is defined as the ratio of the output force Fout (see FIG. 4) to the force input at the ends of the actuation portion 332 (see, e.g., the two actuation forces $F_1$ and $F_2$ in FIG. 4). For example, in some embodiments, the mechanical advantage can be greater than 1. In other embodiments, however, the mechanical advantage can be less than 1, less than 0.8, less than 0.6, less than 0.4, less than 0.2, and any range therebetween.

Although the magnitude the two actuation forces $F_1$ and $F_2$ varies depending on the desired direction of actuation, if the actuating cables (not shown in FIGS. 5-9) attached at the attachment points 336, 337 are connected to a common spool, then as a force is applied to one cable, the force in the opposite cable goes to zero. For example, under this assumption if $F_1$ equals 2 N then $F_2$ is zero. This assumption is used in the derivation of the equations to calculate the mechanical advantage. Thus, the case where $F_1 \geq 0$ and $F_2=0$ will be used to help illustrate the use of the derivations. As such, Fin is equal to $F_1$. However, the derivations are also suited for the case where $F_2 \geq 0$ and $F_1=0$. Mechanical advantage can be calculated using the principle of virtual work. This method provides an equation for $F_1$ as a function of output force Fout and rotation angle $\theta$. After $F_1$ is calculated, the mechanical advantage is given by the ratio of Fout to $F_1$. The first step in calculating the virtual work in the system is choosing a generalized coordinate. The most convenient variable in this case is the rotation angle θ. Next, each of the applied forces ($F_1$ and Fout) are written in vector form. In the derivations that follow, the rotation angle θ is defined to be positive in the counter-clockwise direction (see FIG. 4).

$$F_1 = -F_1 \hat{j} \quad \text{Eq. (16)}$$

$$F_{out} = F_{out}(-\cos(\theta+\alpha)\hat{i} - \sin(\theta+\alpha)\hat{j}) \quad \text{Eq. (17)}$$

Next, position vectors are written from the origin to the placement of the applied forces. As shown in FIG. 7, the origin O is located at the characteristic pivot P, which is half the distance of the flexure length from the fixed point of the flexure.

$$Z_1 = L_1 \cos(\theta)\hat{i} + L_1 \sin(\theta)\hat{j} \quad \text{Eq. (18)}$$

$$Z_{out} = (-L_2 \cos\theta - L_3 \sin\theta)\hat{i} + (-L_2 \sin\theta + L_3 \cos\theta)\hat{j} \quad \text{Eq. (19)}$$

The virtual displacement of the tool member 320 can now be calculated by differentiating the position vectors with respect to the generalized coordinate.

$$\delta Z_1 = (-L_1 \sin\theta \hat{i} + L_1 \cos\theta \hat{j})\delta\theta \quad \text{Eq. (20)}$$

$$\delta Z_{out} = [(L_2 \sin\theta - L_3 \cos\theta)\hat{i} + (-L_2 \cos\theta - L_3 \sin\theta)\hat{j}]\delta\theta \quad \text{Eq. (21)}$$

The virtual work, δW, is calculated by taking the dot product of the force vectors from Eqs. 16 and 17 and the virtual displacement vectors from Eqs. 20 and 21.

$$\delta W_1 = (-F_1 L_1 \cos\theta)\delta\theta \quad \text{Eq. (22)}$$

$$\delta W_{out} = F_{out} L_2[\cos(\theta)\sin(\theta+\alpha) - \sin(\theta)\cos(\theta+\alpha)]\delta\theta + F_{out} L_3[\cos(\theta)\cos(\theta+\alpha) + \sin(\theta)\sin(\theta+\alpha)]\delta\theta \quad \text{Eq. (23)}$$

The virtual work due to the compliance of the flexure must also be accounted for. This is done by first determining the potential energy of the torsional spring (see, e.g., spring 278 in the model for the tool member 220) that is used in the pseudo-rigid-body model.

$$V = \tfrac{1}{2} K(\theta - \theta_o)^2 \quad \text{Eq. (24)}$$

In this equation $\theta_o$ is zero and the torsional spring constant, K, is defined as EI/l. Next, the virtual work is calculated by differentiating the potential energy with respect to the generalized coordinate and multiplying by −δθ.

$$\delta W_{spring} = -K\theta\delta\theta \quad \text{Eq. (25)}$$

The total virtual work in the system is calculated by summing each component of virtual work from Eqs. 22, 23, and 25. Lastly, once the total virtual work is calculated, the principle of virtual work states that if the system is in equilibrium then the virtual work is equal to zero. This can be used to determine $F_1$.

$$\delta W = (-F_1 L_1 \cos\theta)\delta\theta + \\ F_{out} L_2[\cos(\theta)\sin(\theta+\alpha) - \sin(\theta)\cos(\theta+\alpha)]\delta\theta + \\ F_{out} L_3[\cos(\theta)\cos(\theta+\alpha) + \sin(\theta)\sin(\theta+\alpha)]\delta\theta - \frac{EI\theta}{l}\delta\theta = 0 \quad \text{Eq. (26)}$$

$$F_1 = \frac{F_{out}[L_2 \sin\alpha + L_3 \cos\alpha] - \dfrac{EI\theta}{l}}{L_1 \cos\theta} \quad \text{Eq. (27)}$$

In some embodiments, the actuation forces can include a preload (or nonzero forces applied at the first point 336 and the second point 337). In this manner, the amount of backlash in the compliant mechanism can be reduced, thereby allowing improved control over the motion of the first tool member 320 and/or the second tool member 340.

In considering the calculations for the mechanical advantage, if an equal preload force is applied to both sides of the mechanism (i.e., equal preload in both actuation cables) then the input force term, $F_1$, in Eq. 26 is replaced by ($F_1+Fp$) where Fp is the preload force. The virtual work calculations would also need to account for the force at the point of $F_2$ where $F_2=Fp$. This results in a slightly different expression for $F_1$ given by:

$$F_1 = \frac{F_{out}[L_2 \sin\alpha + L_3 \cos\alpha] - \dfrac{EI\theta}{l} + (L_2 - L_1)F_p \cos\theta}{L_1 \cos\theta} \quad \text{Eq. (28)}$$

Because Eqs. 27 and 28 include both geometric boundary conditions and material properties (e.g., Young's Modulus), to calculate the mechanical advantage of the joint mechanism 300, material properties must also be selected. Table 2 includes an example set of material properties used to illustrate the mechanical advantage of a complaint mechanism, such as the joint mechanism 300.

TABLE 2

Material Property Design Boundary Conditions

| Parameter | Value | Notes |
| --- | --- | --- |
| Desired Fout | 0.5 N | |
| E (Young's Modulus) | 95 GPa | Metallic glass material |
| Sy (Yield Strength) | 1800 MPa | Metallic glass material |

Figure 11:
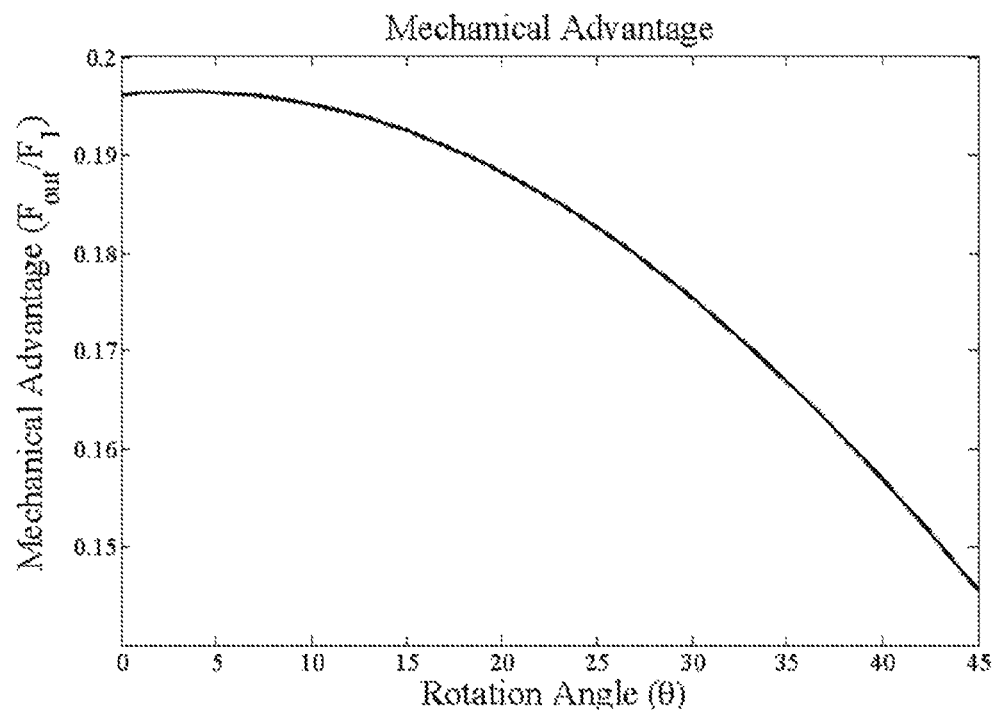
FIG. 11 is a graph showing the calculated mechanical advantage over a range of motion of the tool member shown in FIG. 9.
Figure 12:
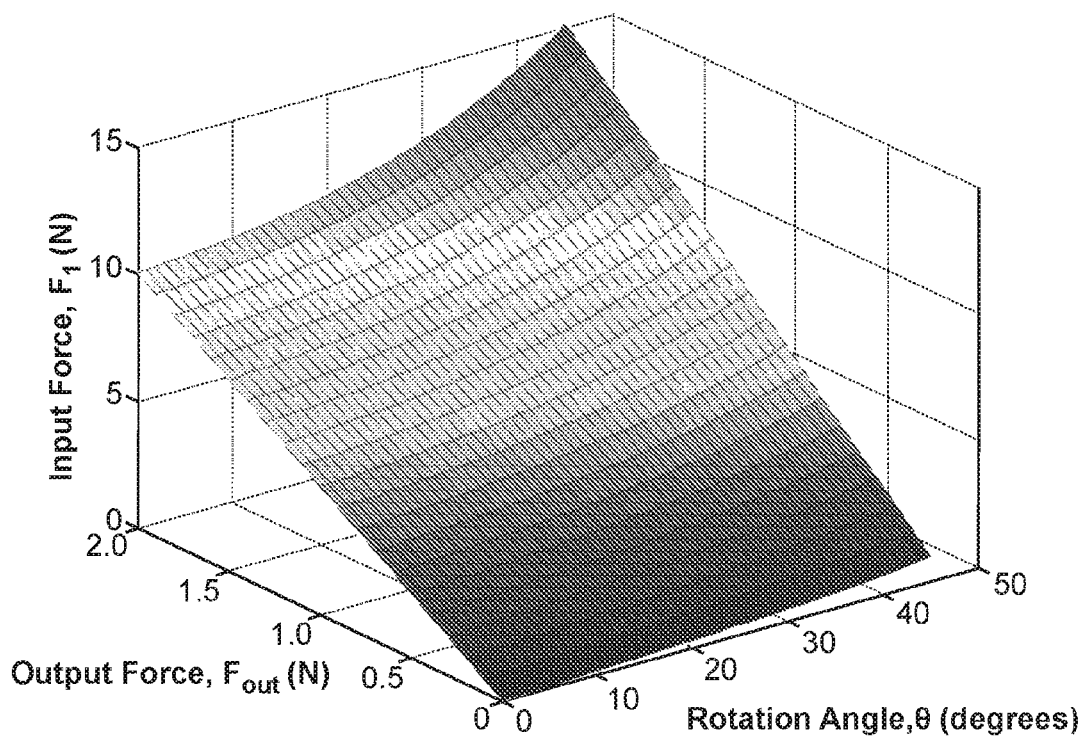
FIG. 12 is a three-dimensional graph showing the calculated input force and output force over a range of motion of the tool member shown in FIG. 9.

FIG. 11 is a plot showing the mechanical advantage for the compliant mechanism 300 as the tool member 320 is actuated to rotate from the undeflected configuration of 0 degrees to 45 degrees. FIG. 12 shows a 3-D "surface" plot of the required input force for a range of output forces from 0 to 2.0 N and a range of rotation of 0 degrees to 45 degrees. Although the calculations and modeling above are described for the joint mechanism 300 with the boundary conditions as provided in Table 1 and the material properties in Table 2, the general results are applicable to any of the compliant joints shown and described herein.

Although Table 1 includes geometric dimensions for one embodiment, in other embodiments, the size and the ratio of various components can be within any suitable range. For example, in some embodiments, the flexure 371 (and any of the flexures shown and described herein) can have any suitable length, width, and thickness to provide the desired resiliency and durability. Specifically, the largest stress within the joint mechanism 300 (or any of the mechanisms described herein) will occur in the flexure 371. The stress in the flexure 371 is a combined result of bending and tension. To determine the desired dimensions and material properties, the magnitude and locations of the maximum stress can be modeled using finite element analysis. Specifically, the joint mechanism 300 having geometric dimensions as set forth in Table 1 and material properties as set forth in Table 2 was modeled using the ANSYS software package.

Figure 13:
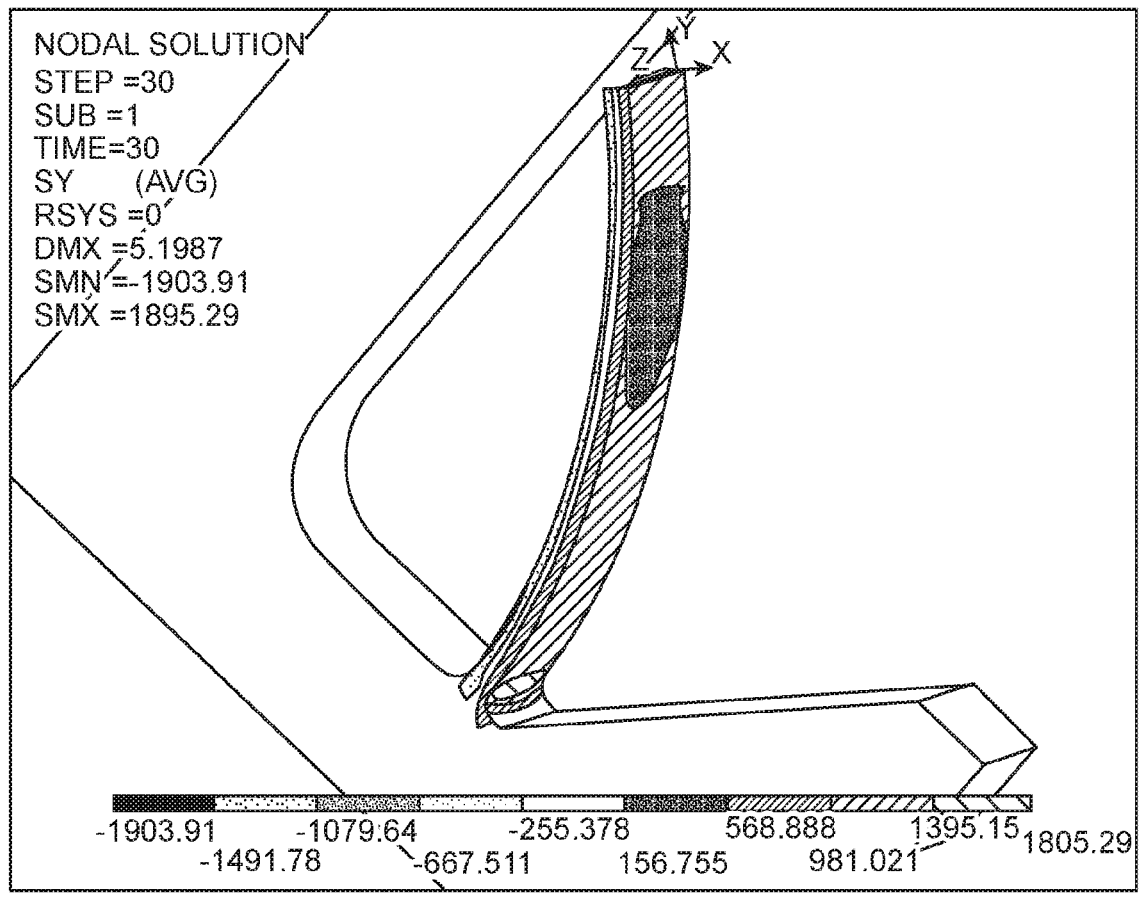
FIG. 13 is a plot of a finite element analysis showing the calculated stress of the tool member shown in FIG. 9 when deflected at an angle of 45 degrees.

FIG. 13 is a plot of a finite element analysis showing the calculated stress of the tool member 320 shown in FIG. 9 when deflected at an angle of 45 degrees, and having an output force of 0.3 N.

Figure 14:
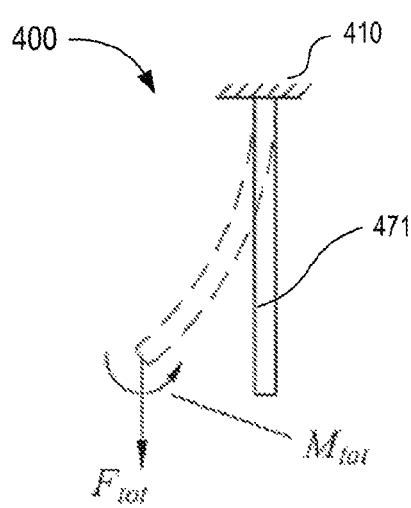
FIGS. 14 and 15 are schematic illustrations of a portion of compliant joint mechanism according to an embodiment, represented as deflected member and a pseudo-rigid-body model, respectively.
Figure 15:
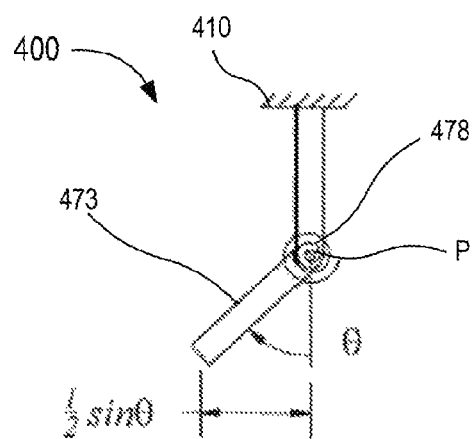

Stress on the flexure 371 (or any of the flexures described herein) can also be calculated using the pseudo-rigid-body model, as described above. Specifically, the combined loading (moment and force) of the flexure is shown in a pseudo-rigid-body model in FIGS. 14 and 15. Specifically, FIG. 14 shows a portion of a mechanism 400 having a flexure 471 that is coupled to a ground 410. The mechanism 400 and the flexure 471 can be similar to any of the mechanisms and flexures, respectively, described herein. As shown in FIG. 14, Mtot is the applied moment and Ftot is the total axial force applied to the flexure 471. FIG. 15 shows the pseudo-rigid-body model of the flexure 471, and shows a spring 478 and pivot point P. To model the deflection, the second end portion 473 of the flexure pivots about the pivot point P, as shown.

The stress within the flexure 471 can be calculated at any spatial location by summing the component of stress due to bending and the component due to axial tension, as shown in Eq. 29:

$$\sigma = \frac{M_{tot} c}{I} + \frac{F_{tot}}{A} \qquad \text{Eq. (29)}$$

where Mtot is the applied moment, c is the distance from the neutral axis to the point of interest, I is the second moment of area about the neutral axis, Ftot is the total axial force, and A is the cross-sectional area of the flexure 471. The total force and moment can be determined by drawing a free-body diagram from the fixed point to the end of the flexure, as shown in FIG. 15. Thus, the total force and moment are given by Eqs. 30 and 31:

$$F_{tot} = F_1 + F_2 + F_{out} \sin(\theta + \alpha) \qquad \text{Eq. (30)}$$

$$M_{tot} = F_2 L_2 \cos\theta - F_1 L_1 \cos\theta + F_{out}\left[L_2 \sin\alpha + \left(L_3 + \frac{l}{2}\right)\cos\alpha\right] \qquad \text{Eq. (31)}$$

Using these equations, the maximum stress within the flexure 471 can be calculated when there is no output force applied. For this example, the dimensions for the flexure 471 (and associated tool member) are the same as those in Table 1. For a particular angle of rotation, for example, θ=−20 degrees, the input force, $F_1$ is calculated from Eq. 27 as 0.290 N. Substituting this value into Eqs. 30 and 31 gives the forces and moments associated with the stress calculations.

$$F_{tot} = 0.290 \text{ N} \qquad \text{Eq. (32)}$$

$$\begin{aligned} M_{tot} &= -0.290(1.30\cos - 20) \qquad \text{Eq. (33)} \\ &= -0.354 \text{ N·mm} \\ &= 0.000354 \text{ N·m} \end{aligned}$$

These values can be substituted into Eq. 34 to calculate the maximum stress in the flexure 471.

$$\sigma_{max} = \frac{(-0.354)\left(\frac{-0.080 \text{ mm}}{2}\right)}{\frac{(0.50 \text{ mm})(0.080 \text{ mm})^3}{12}} + \frac{0.290}{(0.50 \text{ mm})(0.080 \text{ mm})} \qquad \text{Eq. (34)}$$

$$= 671 \text{ MPa}$$

Figure 16:
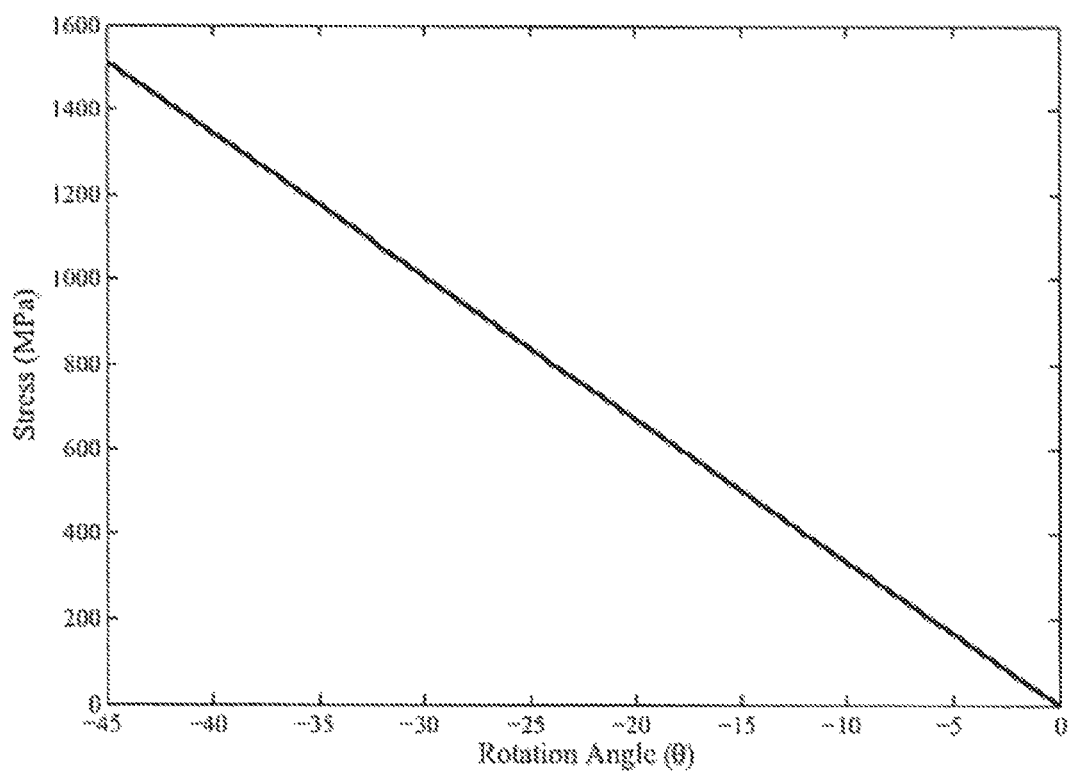
FIG. 16 is a graph showing the calculated stress over a range of motion of the tool member shown in FIGS. 14 and 15.
Figure 17:
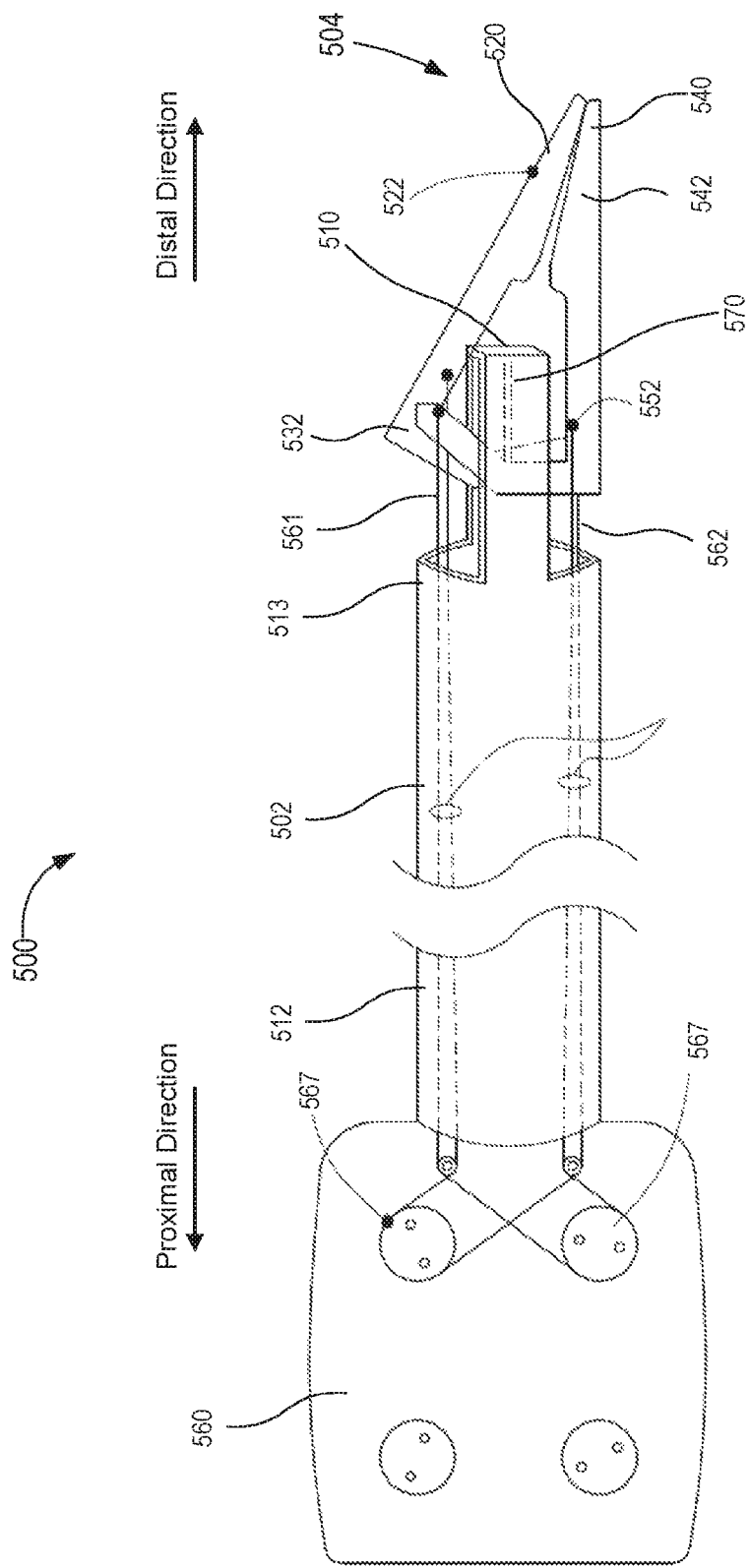
FIG. 17 is a perspective view of a surgical assembly including a compliant joint mechanism, according to an embodiment.

FIG. 16 is a graph showing the calculated stress, based on this modeling, over a range of motion of the tool member shown in FIGS. 14 and 15. Although the calculations and modeling above are described for the compliant mechanism 400 with the boundary conditions as provided in Table 1, the general results are applicable to any of the compliant joints shown and described herein Any of the compliant mechanisms described herein can be used in any suitable surgical assembly or instrument. For example, FIG. 17 shows a schematic illustration of a surgical instrument 500 according to an embodiment. The surgical instrument 500 includes an actuator assembly 560, a shaft 502 and an end effector 504. The actuator assembly 560 includes a series of actuation spools 567 about which a first cable 561 and a second cable 562 are disposed. As described herein, rotational motion of the spools 567 produces actuation forces (e.g., similar to the forces $F_1$ and $F_2$ described above) to actuate the end effector 504.

The shaft 502 has a proximal end portion 512 and a distal end portion 513. The shaft 502 defines a longitudinal axis, along which the distal and proximal directions are defined (see, e.g., the arrows indicating the proximal and the distal direction). The distal end portion 513 of the shaft 502 includes a ground portion 510. The ground portion 510 is a part of, or fixedly coupled to, the shaft 502, and serves as a point of attachment for the first tool member 520 and the second tool member 540 (via the flexure assembly 570).

The end effector 504 includes a first tool member 520, a second tool member 540, and a flexure assembly 570. The instrument 500 or the end effector 504, and any of the joint assemblies described herein, can be used in any suitable surgical device or system as described herein. The first tool member 520 includes an engagement portion 522 and an actuation portion 532. As shown in FIG. 17, the engagement portion 522 is disposed distally from the actuation portion 532, and is configured to exert an engagement force (not shown, similar to the force $F_{OUT}$) on a target structure (not shown). The actuation portion 532 of the first tool member 520 is configured to receive the actuation forces (not shown, but similar to the forces $F_1$ and $F_2$ described above) to actuate the first tool member 520. The actuation forces can be exerted on the actuation portion 532 via the cable 562.

The second tool member 540 includes an engagement portion 542 and an actuation portion 552. As shown in FIG. 17, the engagement portion 542 is disposed distally from the actuation portion 552, and is configured to exert an engagement force (not shown, similar to the force $F_{OUT}$) on a target structure (not shown). The actuation portion 552 of the second tool member 540 is configured to receive the actuation forces (not shown, but similar to the forces $F_1$ and $F_2$ described above) to actuate the second tool member 540. The actuation forces can be exerted on the actuation portion 552 via the cable 561.

The first tool member 520 and the second tool member 540 are coupled to the ground portion 510 via the flexure assembly 570. The flexure assembly 570 can include any suitable flexure or assembly of flexures to facilitate movement of the first tool member 520 and the second tool member 540 as described herein with respect to any of the compliant mechanisms shown. As shown, the flexure assembly 570 is positioned such that the first tool member 520 and the second tool member 540 are each coupled to the shaft 502 in a manner that produces an inverted configuration.

Figure 18:
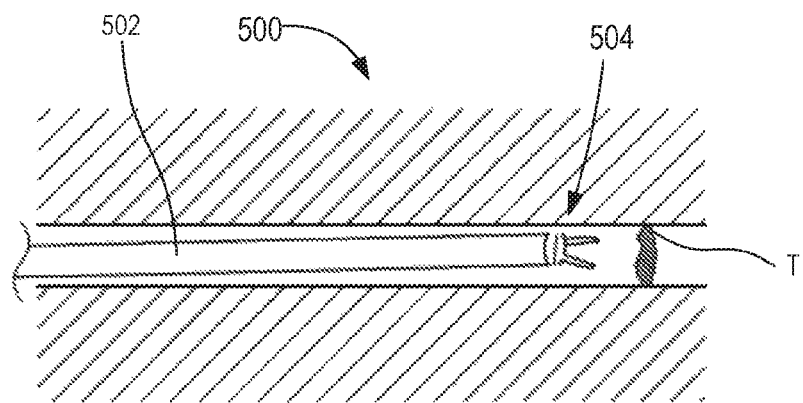
FIGS. 18 and 19 are side views of the surgical assembly shown in FIG. 17 in various operating configurations.
Figure 19:
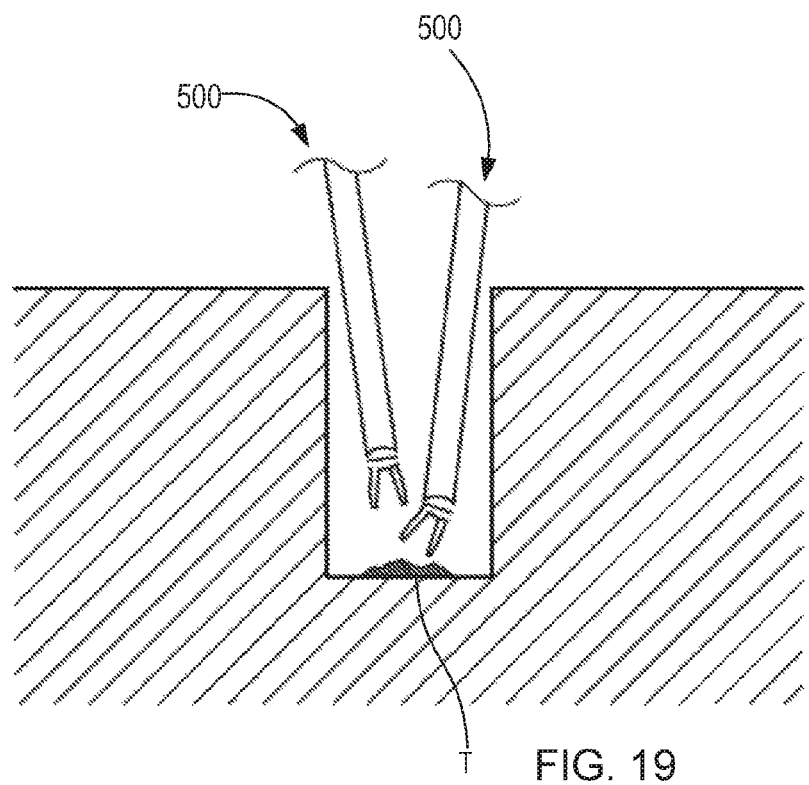

In use, the surgical instrument 500 can be used in any number of scenarios. For example, FIG. 18 shows a portion of the instrument 500 approaching a target structure T within a long, narrow lumen. FIG. 19 shows a pair of instruments 500 approaching a target structure T within a wider lumen that has restricted access at the bottom of the lumen.

Although the joint mechanism 300 and the modeling thereof was described for a range of motion of between ±45 degrees, in some embodiments, a compliant joint mechanism can have any suitable range of motion. Moreover, although the joint mechanism 300 is shown as having a decreasing mechanical advantage as the angle of rotation increases (see, e.g., FIG. 11), in other embodiments, a compliant joint mechanism can have a substantially constant mechanical advantage of its range of motion. For example, in some embodiments, a compliant joint mechanism can be configured such that the mechanical advantage varies by less than 20 percent over its range of motion (e.g. of 90 degrees). This arrangement permits a wider operating range through which grasping, cutting, and manipulating can be performed. Moreover, in some embodiments, a tool member can include an actuation portion that receives an actuation force in a manner that maintains a substantially constant moment arm throughout the range of motion. By maintaining a substantially constant moment arm, the actuation force can remain effective to rotate the tool member throughout a wide angular range.

For example, FIGS. 20-31 are various views of a compliant joint mechanism 600 (also "joint mechanism 600" or "compliant mechanism 600") according to an embodiment. The joint mechanism 600 includes a shaft 602 having a ground member 610, a first tool member 620, a second tool member 640, and a first flexure assembly 670, and a second flexure assembly 680. The first tool member 620 and the second tool member 640 can be a portion of an end effector 604 for a surgical instrument, such as the instrument 500. The joint mechanism 600 can be used in any suitable surgical device or system as described herein.

The shaft defines a longitudinal axis along which the distal and proximal directions are defined. The distal end portion of the shaft 602 defines an opening (slot) 615 that allows the tool member to rotate through the desired range of motion. The distal end portion of the shaft 602 also includes a mounting portion 614 to which the ground member 610 is fixedly coupled. As shown in FIGS. 22 and 23, the mounting portion 614 defines a pair of slots 606 that receive the ground member 610.

The ground member 610 is fixedly coupled to the shaft 602, and serves as a point of attachment for the first tool member 620 and the second tool member 640 (via the first flexure assembly 670 and the second flexure assembly 680, respectively). The ground member 610 includes a first end portion 616, a second end portion 618, and a central portion 617 therebetween. Each of the first end portion 616 and the second end portion 618 are disposed within their respective mounting slot 606. The central portion 617 is raised from the first end portion 616 and the second end portion 618 (i.e., the ground member 610 has an offset shape). As shown in FIG. 23, the central portion 617 defines a series of openings 619 that mount the first flexure assembly 670 and the second flexure assembly 680 to the ground member 610.

Figure 28:
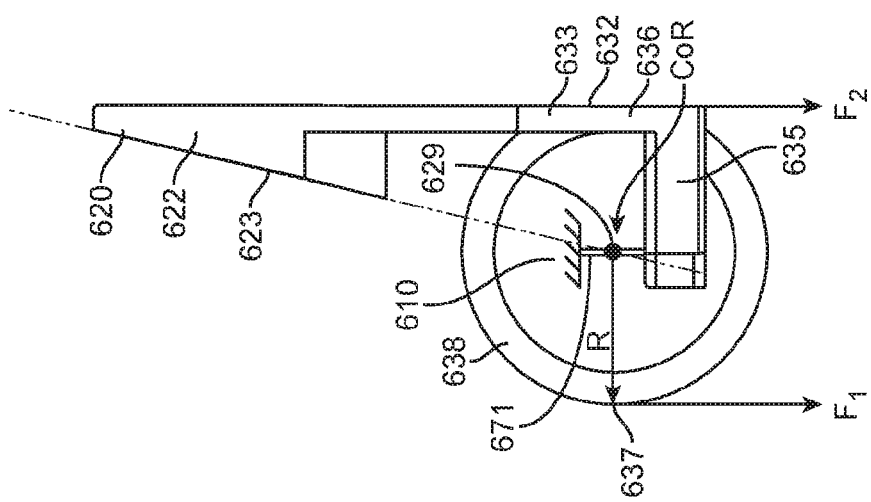
FIG. 28 is a front view of the surgical assembly shown in FIGS. 20 and 21, shown schematically to illustrate the input forces and center of rotation.
Figure 31:
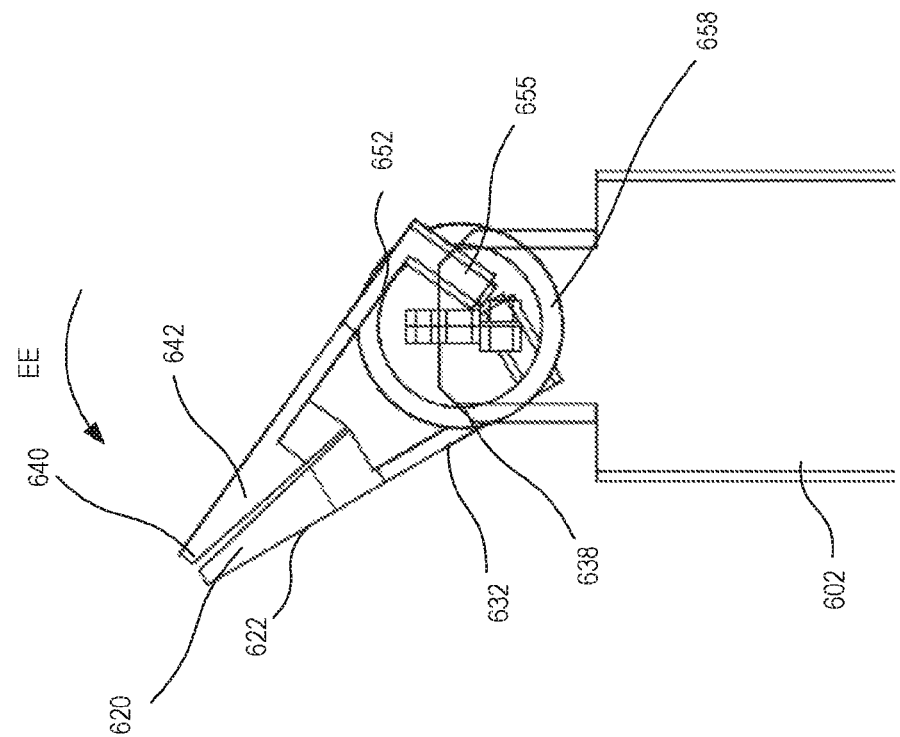
Figure 30:
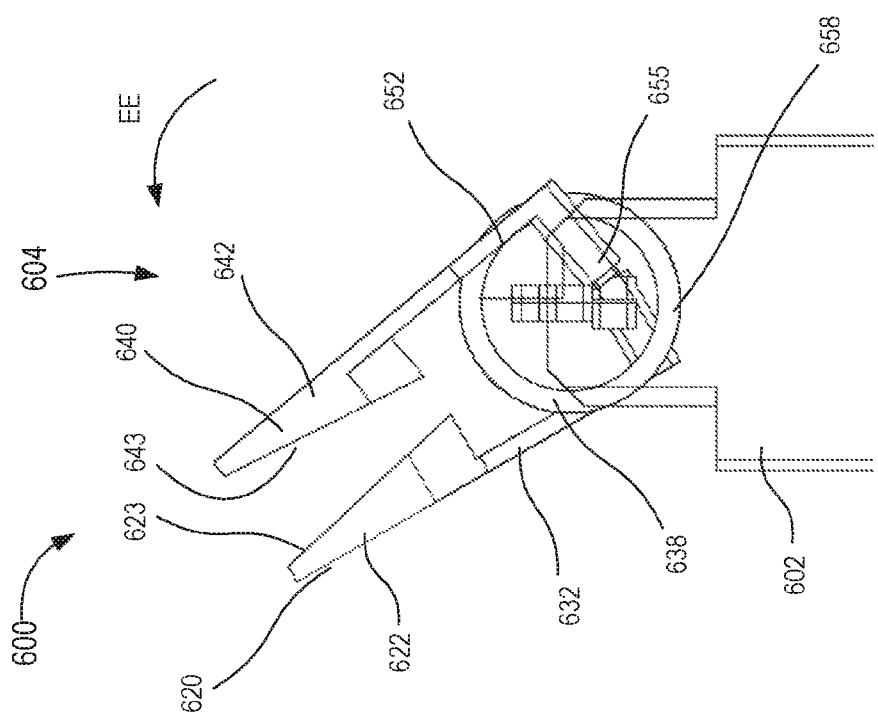

The first tool member 620 includes an engagement portion 622 and an actuation portion 632. The engagement portion 622 is disposed distally from the actuation portion 632, and is configured to exert an engagement force (not shown, similar to the force $F_{OUT}$ shown in FIG. 4) on a target structure (not shown). Specifically, the engagement portion 622 includes an engagement surface 623. Moreover, as shown in FIG. 28, the engagement surface 623 defines an engagement plane (indicated by the dashed line in FIG. 28). As described herein, the engagement plane intersects the characteristic pivot point (identified as CoR in FIG. 28). Moreover, the engagement plane can intersect the pivot point over the entire range of angular motion of the first tool member 620. This arrangement allows the engagement surface 623 and the engagement surface 643 to remain parallel to ("flush with") each other when the first tool member 620 and the second tool member 640 close upon each other throughout the range of motion.

The actuation portion 632 of the first tool member 620 is configured to receive the actuation forces (see the forces $F_1$ and $F_2$ in FIG. 28) to actuate the first tool member 620. The actuation portion 632 includes a longitudinal portion (or arm) 633, a lateral portion (or arm) 635, and a spool 638 (also referred to as a pulley). The longitudinal arm 633 is substantially parallel to the longitudinal axis of the shaft 602 when the first tool member 620 is in the undeflected configuration (see FIG. 25). The longitudinal arm 633 defines a slot 634 through which the cable 661 passes. The lateral arm 635 is substantially normal to the longitudinal axis of the shaft 602 when the first tool member 620 is in the undeflected configuration (see FIG. 25). Although the lateral arm 635 is normal to the longitudinal arm 633, in other embodiments, the lateral arm 635 can form any angle with the longitudinal arm 633. The lateral arm 635 defines two openings 605 that mount the first flexure assembly 670 to the first tool member 620.

Figure 21:
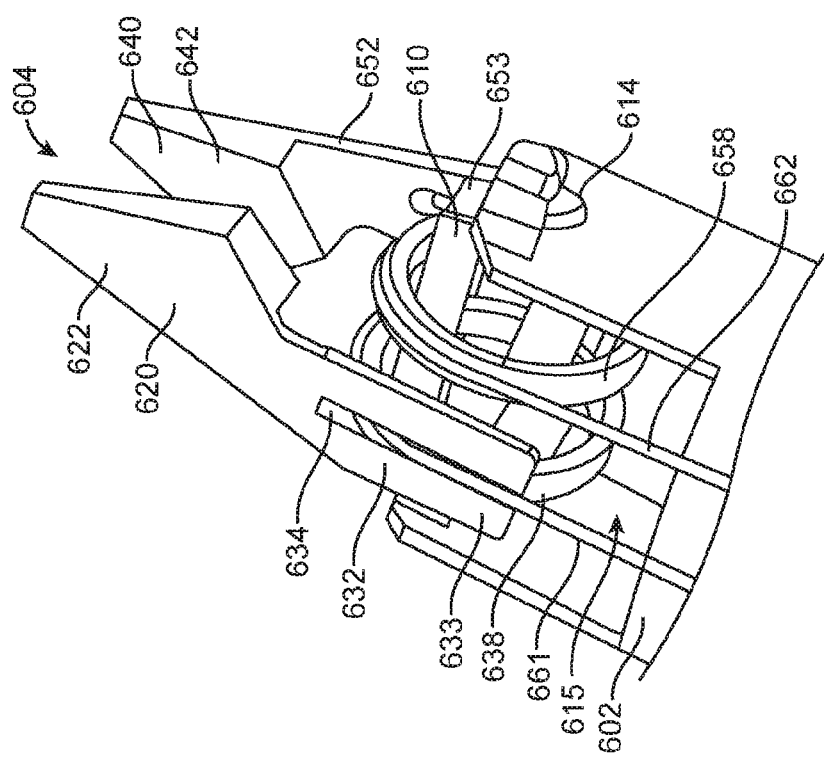
FIGS. 20 and 21 are perspective views of a surgical assembly including a compliant joint mechanism, according to an embodiment.
Figure 20:
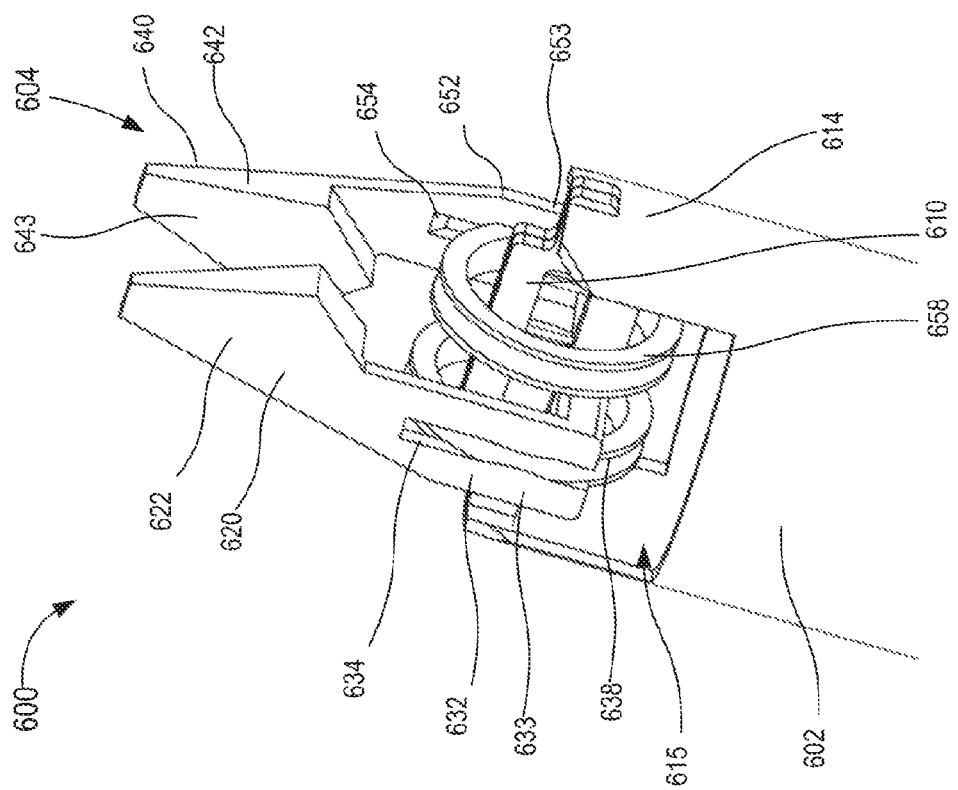
Figure 27:
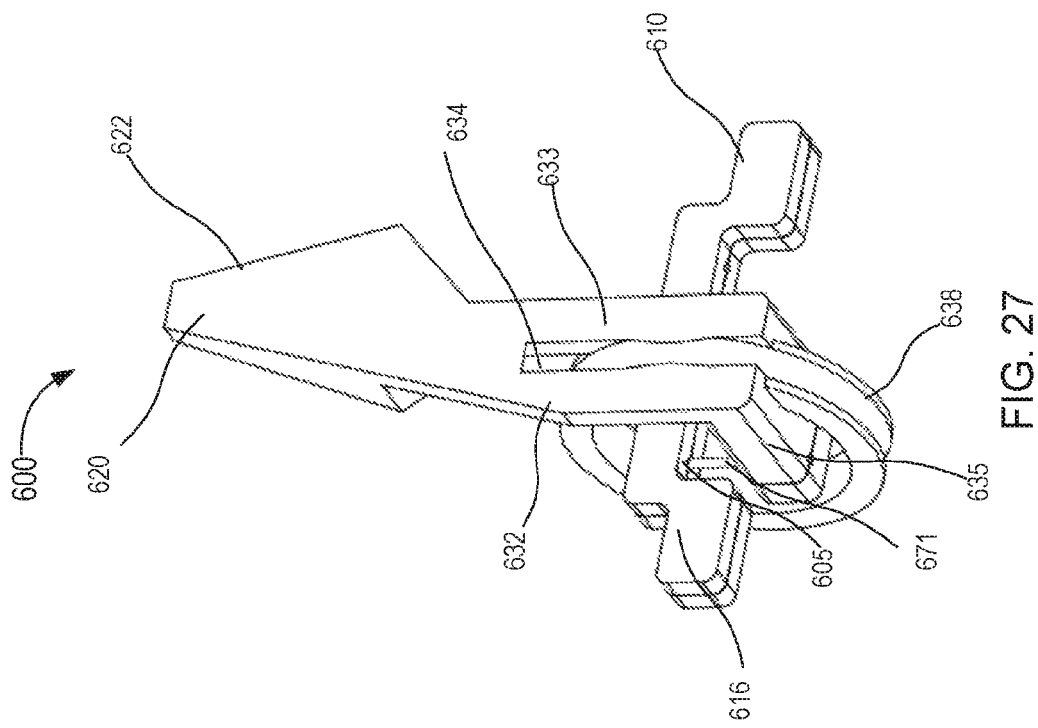
FIGS. 26 and 27 are perspective views of a portion of the surgical assembly shown in FIGS. 20 and 21.
Figure 26:
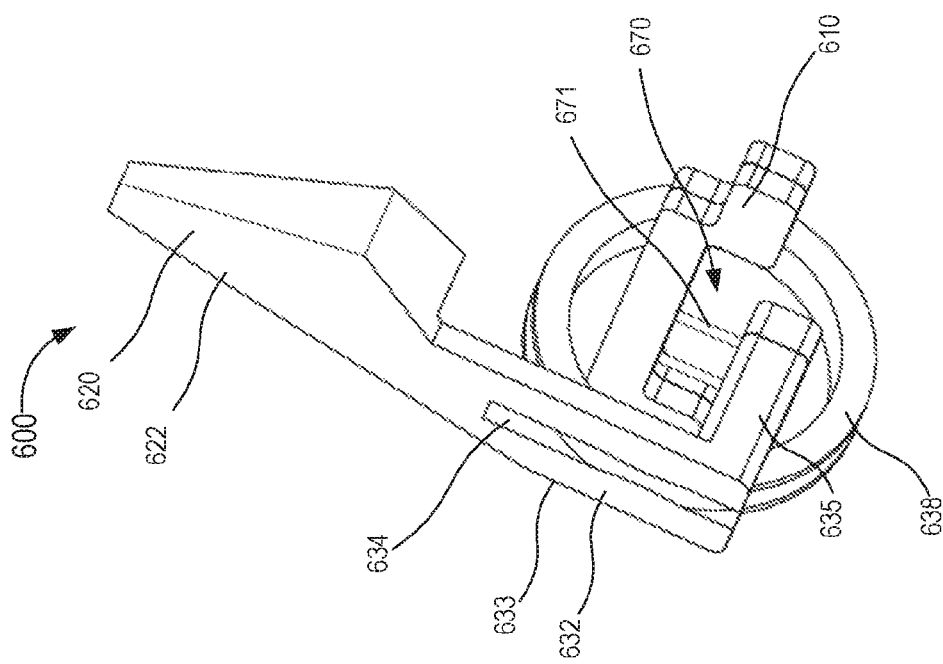
Figure 29:
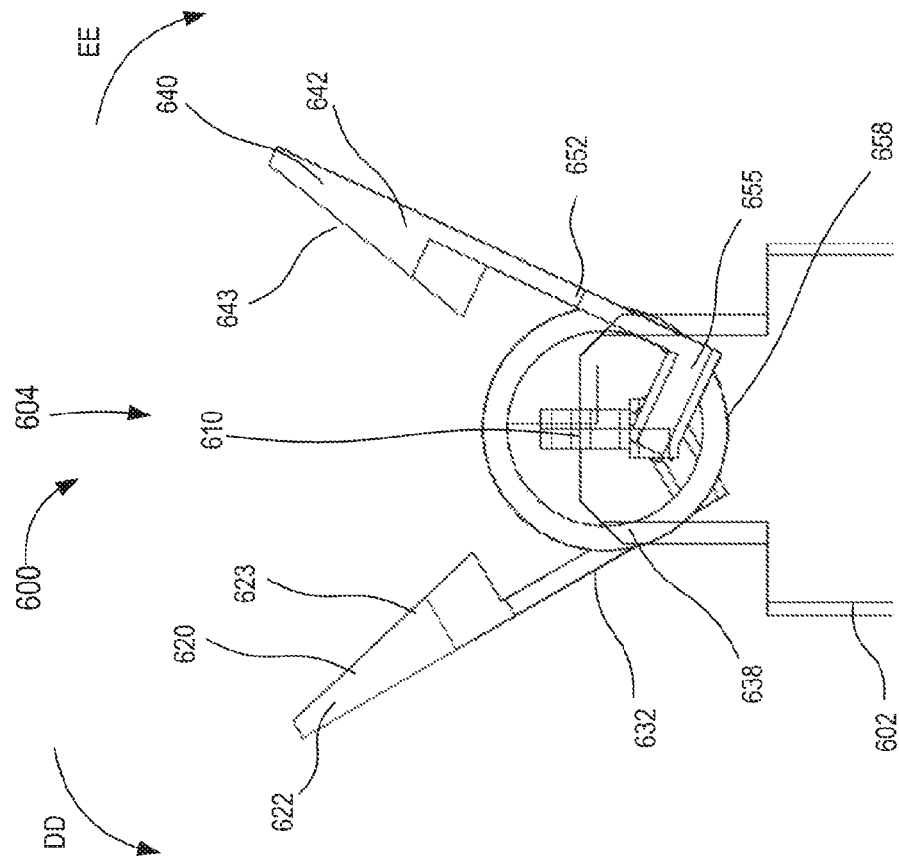
FIGS. 29-31 are front views of the surgical assembly shown in FIGS. 20 and 21, in a second configuration, a third configuration, and a fourth configuration, respectively.

The actuation forces can be exerted on the actuation portion 632 by the cable 661 shown in FIG. 21. Specifically, the actuation forces can be exerted along the tangent points to the spool 638. As shown in FIG. 28, the spool 638 is a circular shaped member having a radius R. In use, the cable 661 exerts the actuation forces $F_1$ and $F_2$ at a first attachment point 636 and a second attachment point 637, respectively. Because the actuation forces are exerted along the surface of the circular spool 638, as the first tool member 620 rotates, the moment distance remains substantially constant. Similarly stated, because the actuation forces are not exerted at a fixed location on the actuation portion 632, the attachment points remain spaced apart from the pivot point (in a direction normal to the longitudinal axis of the shaft 602) by a substantially constant moment distance. This arrangement allows the mechanical advantage to remain substantially constant throughout the angular range of motion of the first tool member 620.

Although the moment distance between the attachment points 636, 637 and the pivot point CoR is described as being substantially constant throughout the angular range of motion of the first tool member 620, in other embodiments, the moment distance can vary by less than ten percent. In other embodiments, the moment distance can vary by less than twenty percent.

The second tool member 640 includes an engagement portion 642 and an actuation portion 652. The engagement portion 642 is disposed distally from the actuation portion 652, and is configured to exert an engagement force (not shown, similar to the force $F_{OUT}$ shown in FIG. 4) on a target structure (not shown). Thus, the first tool member 620 and the second tool member 640 can together (or collectively) exert an engagement force on the target structure that is located between the engagement portion 622 and the engagement portion 642. Specifically, the engagement portion 642 includes an engagement surface 643. Moreover, as shown in FIG. 28 with respect to the engagement surface 623, the engagement surface 643 also defines an engagement plane that intersects the characteristic pivot point (identified as CoR in FIG. 28). Moreover, the engagement surface 643 can intersect the pivot point over the entire range of angular motion of the second tool member 640. This arrangement allows the engagement surface 623 and the engagement surface 643 to remain parallel to ("flush with") each other when the first tool member 620 and the second tool member 640 close upon each other throughout the range of motion (see e.g., FIG. 31).

The actuation portion 652 of the second tool member 640 is configured to receive the actuation forces (see the forces $F_1$ and $F_2$ in FIG. 28) to actuate the second tool member 640. The actuation portion 652 includes a longitudinal portion (or arm) 653, a lateral portion (or arm) 655, and a spool 658 (also referred to as a pulley). The longitudinal arm 653 is substantially parallel to the longitudinal axis of the shaft 602 when the second tool member 640 is in the undeflected configuration (see FIG. 25). The longitudinal arm 653 defines a slot 654 through which the cable 662 passes. The lateral arm 655 is substantially normal to the longitudinal axis of the shaft 602 when the second tool member 640 is in the undeflected configuration (see FIG. 25). Although the lateral arm 655 is normal to the longitudinal arm 653, in other embodiments, the lateral arm 655 can form any angle with the longitudinal arm 653. The lateral arm 655 defines two openings 651 that mount the second flexure assembly 680 to the second tool member 640. The actuation forces can be exerted on the actuation portion 652 by the cable 662 shown in FIG. 21.

The actuation forces can be exerted on the actuation portion 652 by the cable 662 shown in FIG. 21. Specifically, the actuation forces can be exerted along the tangent points to the spool 658. As shown in FIG. 28 with respect to the first tool member 620, the spool 658 is also a circular shaped member having a radius R. In use, the cable 662 exerts the actuation forces at attachment points that are along the surface of the circular spool 658. Thus, as described above, when the second tool member 640 rotates, the moment distance remains substantially constant. Similarly stated, because the actuation forces are not exerted at a fixed location on the actuation portion 652, the attachment points remain spaced apart from the pivot point (in a direction normal to the longitudinal axis of the shaft 602) by a substantially constant moment distance. This arrangement allows the mechanical advantage to remain substantially constant throughout the angular range of motion of the second tool member 640.

The first tool member 620 and the second tool member 640 are coupled to the ground portion 610 via the first flexure assembly 670 and the second flexure assembly 680, respectively. The first flexure assembly 670 includes a pair of flexures 671. Each of the flexures 671 has a first end portion that is coupled within a respective opening 619 defined by the ground member 610. Each of the flexures 671 has a second end portion that is coupled within a respective opening 605 defined by the lateral arm 635. In this manner, the first tool member 620 is coupled to the shaft 602 in a manner that produces an inverted configuration, as described above. As shown, the first flexure assembly 670 is disposed between the engagement portion 622 and a proximal-most surface of the actuation portion 632. Moreover, the first tool member 620 is coupled to the shaft 602 such that the ground member 610 is disposed between the engagement portion 622 and the proximal-most surface of the actuation portion 632.

The second flexure assembly 680 includes a pair of flexures 681. Each of the flexures 681 has a first end portion that is coupled within a respective opening 619 defined by the ground member 610. Each of the flexures 681 has a second end portion that is coupled within a respective opening 651 defined by the lateral arm 655. In this manner, the first tool member 620 is coupled to the shaft 602 in a manner that produces an inverted configuration, as described above. As shown, the second flexure assembly 680 is disposed between the engagement portion 642 and a proximal-most surface of the actuation portion 652. Moreover, the second tool member 640 is coupled to the shaft 602 such that the ground member 610 is disposed between the engagement portion 642 and the proximal-most surface of the actuation portion 652.

As described above with reference to the joint mechanisms 200 and 300, the flexures 671 are configured to deform elastically when the actuation forces are exerted on the actuation portion 632 of the first tool member 620 such that the first tool member 620 rotates relative to the shaft. This rotation is shown by the arrow DD in FIGS. 25 and 29. The rotational motion can be modeled using the PRBM, which, as described above, models the flexures 671 as a pin joint rotating about a characteristic pivot. Referring to FIG. 28, the characteristic pivot is identified as CoR. The characteristic pivot is also coaxial with a central axis 629 (also referred to as the axis of rotation) of the spool 638 (see e.g., FIG. 24). Thus, when the first tool member 620 is actuated, it rotates about the characteristic pivot CoR and the central axis 629. Moreover, as described above, the spool 638 and the spool 658 are configured to produce a substantially constant moment distance through the angular range of motion of the first tool member 620 and the second tool member 640, respectively. The range of motion for the first tool member 620 and the second tool member 640 can be within ±30 degrees, ±45 degrees, ±60 degrees, ±75 degrees, ±90 degrees, or greater than ±90 degrees.

FIGS. 25, 29-31 show the joint mechanism 600 in a first configuration, second configuration, third configuration, and fourth configuration respectively. As shown, the first tool member 620 and the second tool member 640 can rotate about the shaft 602 independently of each other. Thus, the compliant joint mechanism 600 has two degrees of freedom (both wrist motion and gripping motion). Moreover, the range of motion for the first tool member 620 and the second tool member 640 can be within ±30 degrees, ±45 degrees, ±60 degrees, ±75 degrees, ±90 degrees, or greater than ±90 degrees. Specifically, because the actuation cables 661 and 662 are confined with the grooves of the spool 638 and the spool 658, respectively, the moment distance throughout the entire range of motion remains substantially constant. Thus, the mechanical advantage (and therefore the performance) of the compliant joint mechanism 600 is consistent throughout the entire range of motion.

To assess the impact of the spool 638, 658 on the mechanical advantage of the joint mechanism 600 over its range of angular motion, a mechanical advantage analysis was completed. The analysis compared the mechanical advantage profile of a tool member without a spool (similar to the tool member 220) against the mechanical advantage profile of a tool member including a spool (similar to the tool member 620). Specifically, FIGS. 32A and 32B show a tool member 220' (which has a fixed attachment point) and FIGS. 33A and 33B show a tool member 620" (which includes a spool 638").

Figure 32B:
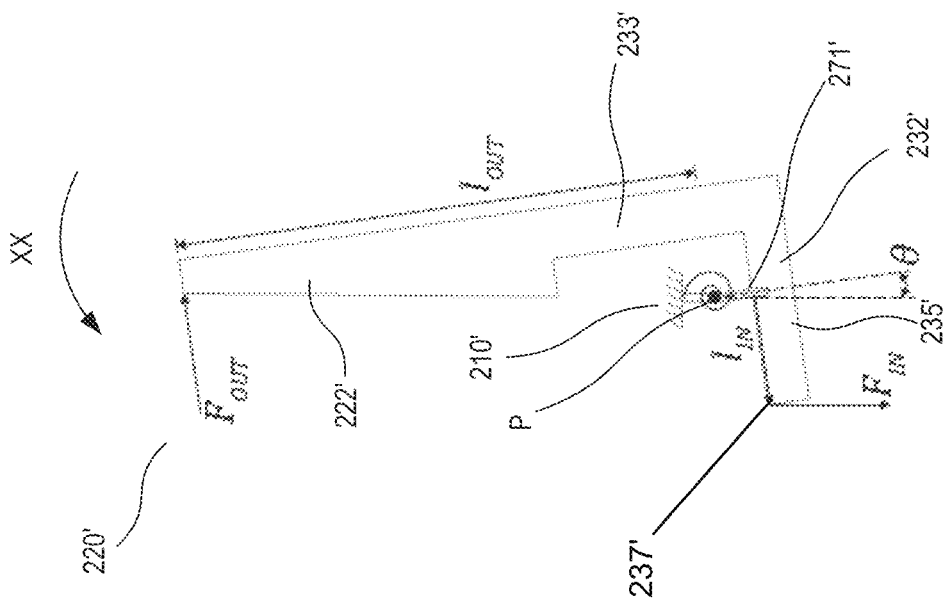
FIGS. 32A and 32B are schematic illustrations of a tool member having an "L-arm" shape according to an embodiment, for modeling purposes.
Figure 32A:
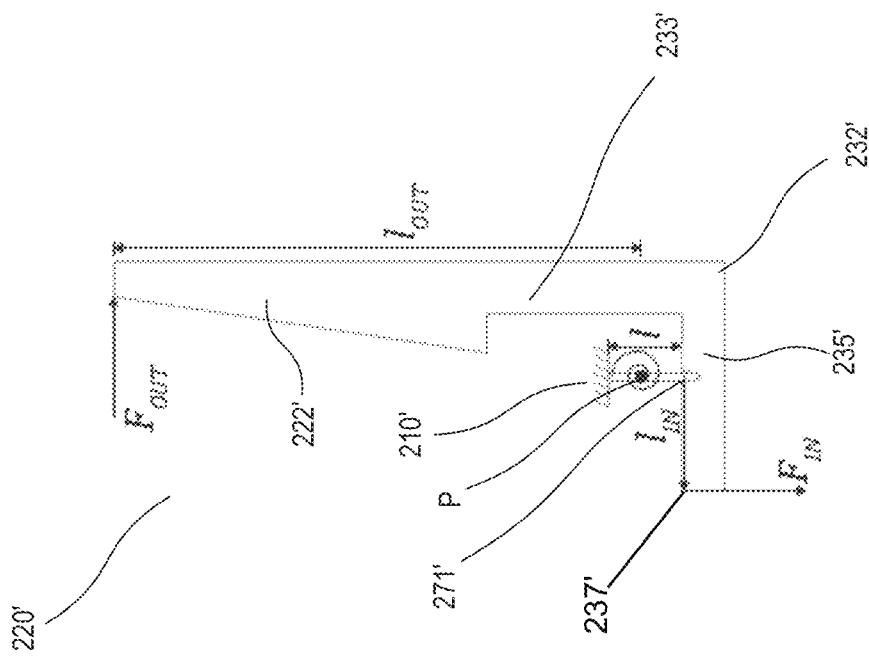
Figure 33B:
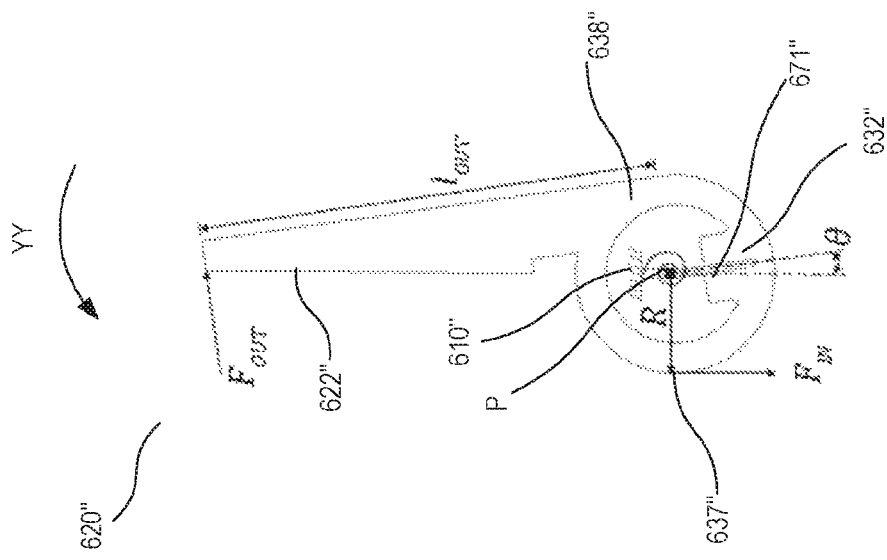
FIGS. 33A and 33B are schematic illustrations of a tool member having a spool design according to an embodiment, for modeling purposes.
Figure 33A:
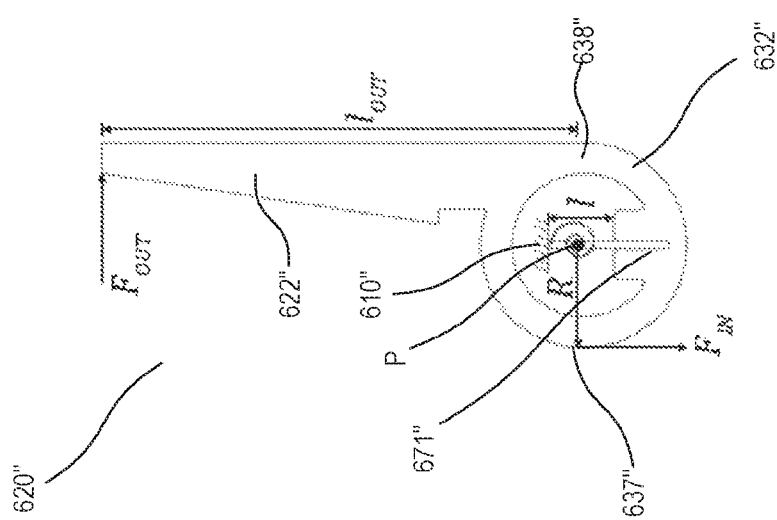

Referring to FIGS. 32A and 32B, the tool member 220' includes an engagement portion 222' and an actuation portion 232'. The engagement portion 222' is disposed distally from the actuation portion 232', and is configured to exert an engagement force $F_{OUT}$ on a target structure (not shown). The actuation portion 232' is configured to receive the actuation force $F_{IN}$ to actuate the first tool member 220'. The actuation portion 232' includes a longitudinal portion (or arm) 233', a lateral portion (or arm) 235', and includes a connection point 237' at which the actuation force $F_{IN}$ is applied. The lateral arm 235' is coupled to a flexure 271' that is, in turn, coupled to a ground 210'. The flexure 271' is configured to deform elastically when the actuation force $F_{IN}$ is exerted on the actuation portion 232' such that the tool member 220' rotates relative to the ground 210', as shown by the arrow XX. This is modeled using the PRBM as showing the tool member 220' rotating about the characteristic pivot P by an angle of θ.

For the L-Arm without a spool (as shown in FIGS. 32A and 32B), the mechanical advantage calculations are described below. First, the sum of the moments about the approximate center of rotation is:

$$F_{in}\left(l_{in}\cos(\theta) - \frac{l}{2}\sin(\theta)\right) = T + F_{out}l_{out} \quad \text{Eq. (35)}$$

Where $F_{IN}$ is the input force, Fin is the perpendicular distance from the flexure 271' to the point at which the input force is applied (the connection point 237'), θ is the angular deflection from the nominal (undeflected) state, T is the torque due to the modeled torsional spring at the center (pivot point P) of the flexure 271', $F_{OUT}$ is the output force at the tip of the jaw (or engagement portion 222'), and/out is the perpendicular distance from center of rotation (P) to the output force $F_{OUT}$. For this analysis/in is equal to the radius of the pulley, R, used in the analysis of the L-Arm mechanism with an integrated spool (see FIGS. 33A and 33B). Using the pseudo-rigid-body model, the SFLP assumption the flexure is modeled as a pin joint with a torsional spring at the mid-length of the flexure 271'. The torque, T, due to the torsional spring is defined as:

$$T = \frac{EI}{l}\theta \quad \text{Eq. (36)}$$

Where E is the modulus of elasticity of the flexure, I is the second moment of area, and I is the flexure length. Substituting Eq. 36 into Eq. 35 and solving for the mechanical advantage, $F_{OUT}/F_{IN}$, results in the following:

$$MA_{np} = \left(\frac{1}{l_{in}\cos(\theta) - \frac{l}{2}\sin(\theta)}\left(\frac{EI\theta}{F_{out}l} + l_{out}\right)\right)^{-1} \quad \text{Eq. (37)}$$

Where MAnp is the mechanical advantage of the L-Arm mechanism without the integrated spool.

Referring to FIGS. 33A and 33B, the tool member 620" includes an engagement portion 622" and an actuation portion 632". The engagement portion 622" is disposed distally from the actuation portion 632", and is configured to exert an engagement force $F_{OUT}$ on a target structure (not shown). The actuation portion 632" is configured to receive the actuation force $F_{IN}$ to actuate the first tool member 620". The actuation portion 632" includes spool 638', which defines a connection point 637" at which the actuation force $F_{IN}$ is applied. The actuation portion 632" is coupled to a flexure 671" that is, in turn, coupled to a ground 610". The flexure 671" is configured to deform elastically when the actuation force $F_{IN}$ is exerted on the actuation portion 632" such that the tool member 620" rotates relative to the ground 610", as shown by the arrow YY. This is modeled using the PRBM as showing the tool member 620" rotating about the characteristic pivot P by an angle of θ.

For the tool member 620", the sum of the torques about the approximate center of rotation P is:

$$F_{in}R = T + F_{out}l_{out} \quad \text{Eq. (38)}$$

Where R is the radius of the spool 638'. Solving for the mechanical advantage, $F_{OUT}/F_{IN}$, results in the following $$MA_p = \left(\frac{T}{F_{out}R} + \frac{l_{out}}{R}\right)^{-1} \quad \text{Eq. (39)}$$

Where MAnp is the mechanical advantage of the tool member 620" with the integrated spool 638". Substituting Eq. 36 into Eq. 39 results in the following:

$$MA_p = \left(\frac{EI\theta}{F_{out}Rl} + \frac{l_{out}}{R}\right)^{-1} \quad \text{Eq. (40)}$$

Figure 34:
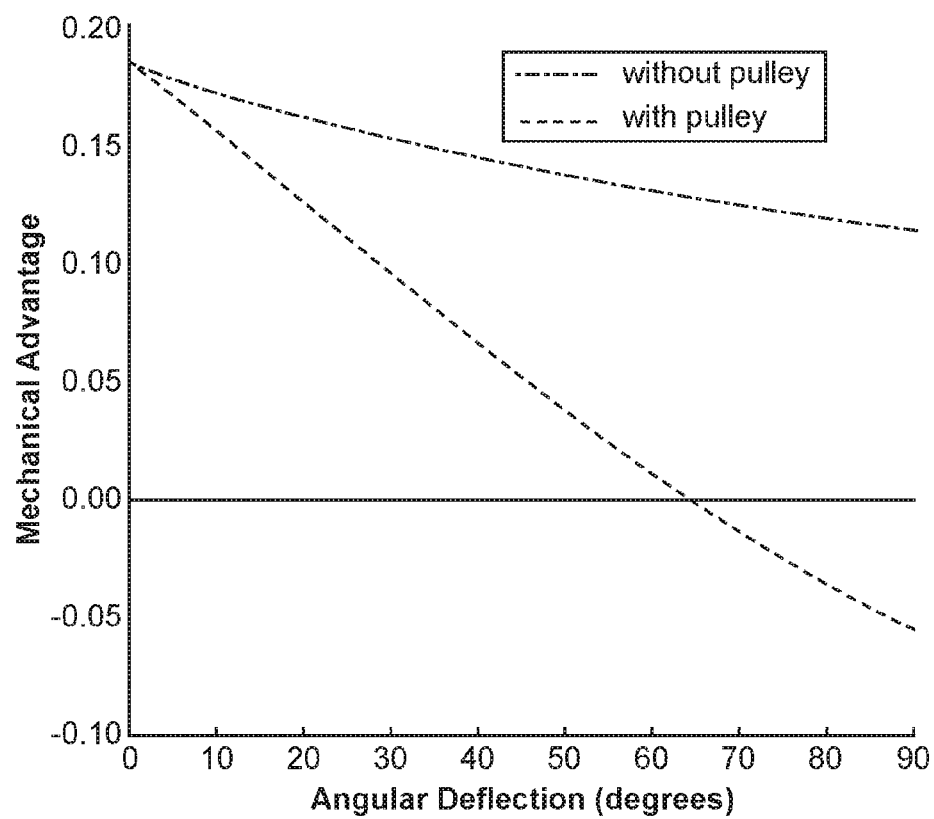
FIG. 34 is a graph showing the calculated mechanical advantage over a range of motion of the tool members shown in FIGS. 32A-32B and 33A-33B.

Using the values in Table 3, below, the mechanical advantage for the L-Arm with and without the integrated spool was calculated as a function of angular deflection. FIG. 34 shows the mechanical advantage for a 3 mm L-Arm with the spool (e.g., tool member 620") and without the spool (e.g., tool member 220'). Titanium was used for simplicity in the model. The material modulus of elasticity will only affect the shape of the curve, not the point at which the mechanical advantage becomes negative (for the L-Arm without a spool). The point at which the curve crosses zero is dictated by the effective moment arm for the input force, Fin. The plot also shows that the mechanical advantage of the L-Arm design with a spool has less variation compared to the L-Arm without a spool, and it never becomes negative. In some embodiments, a tool member (e.g., the tool member 220 or 220') without a spool can be actuated via cables up to 65 degrees before the mechanical advantage reaches zero. In contrast, in some embodiments, a tool member (e.g., the tool member 620 or 620") with a spool can be actuated over the desired range of motion, e.g., 90 degrees. Although the mechanical advantage is less than 1 for both designs shown, in some embodiments, electric motors can develop the torques necessary to obtain the desired output force at the tip of the instrument.

In some embodiments, the flexure 671 (and any of the flexures shown and described herein) can have any suitable length, width, and thickness to provide the desired resiliency and durability. Specifically, the largest stress within the compliant mechanism 600 (or any of the mechanisms described herein) will occur in the flexure 671. The stress in the flexure 671 is a combined result of bending and tension. To determine the desired dimensions and material properties, the magnitude and locations of the maximum stress can be modeled using finite element analysis. Specifically, the compliant mechanism 600 having geometric dimensions and material properties as set forth in Table 3 was modeled using the ANSYS software package.

TABLE 3

Geometric and Material Property Design Boundary Conditions

| Parameter | Value | Property | Value |
|---|---|---|---|
| Flexure length | 1.25 mm | E (Young's Modulus) | 44.0 GPa |
| Flexure thickness | 0.102 mm | μ | 0.3 |

TABLE 3-continued

Geometric and Material Property Design Boundary Conditions

| Parameter | Value | Property | Value |
|---|---|---|---|
| Flexure width | 0.25 mm | $\sigma^{AS}_s$ | 440 MPa |
| | | $\sigma^{AS}_f$ | 472 MPa |
| | | $\sigma^{SA}_s$ | 218 MPa |
| | | $\sigma^{SA}_f$ | 206 MPa |
| | | $\varepsilon_L$ | 0.045 |
| | | $\alpha$ | 0 |

For the purposes of modeling, and for the fabrication of prototype versions of the compliant joint mechanism 600, NiTi was selected for the flexure 671. Although superelastic NiTi is commercially available in form factors including wire, rod, tubing, strip and sheet, a NiTi strip of 0.102~mm (the smallest thickness available) and was used in the modeling described herein. Referring to Table 3, E is the modulus of elasticity of the NiTi in the austenite phase, μ is Poisson's ratio, $\sigma^{AS}_s$ is the starting stress value of the forward phase transformation, $\sigma^{AS}_f$ is the final stress value of the forward phase transformation, $\sigma^{SA}_s$ is the starting stress value of the reverse phase transformation, $\sigma^{SA}_f$ is the final stress value of the reverse phase transformation, EL is the maximum residual strain, and a is the material response ratio between tension and compression.

Figure 35:
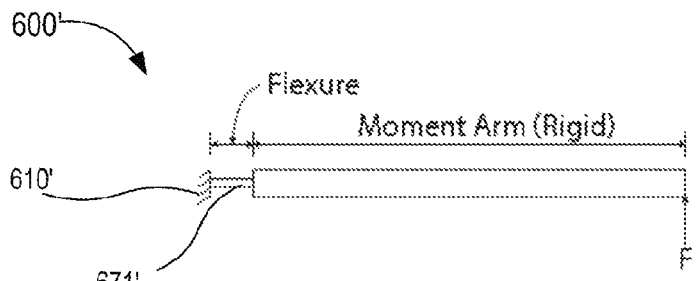
FIG. 35 is a schematic illustration of a portion of the surgical assembly shown in FIGS. 20 and 21, for modeling purposes.
Figure 36:
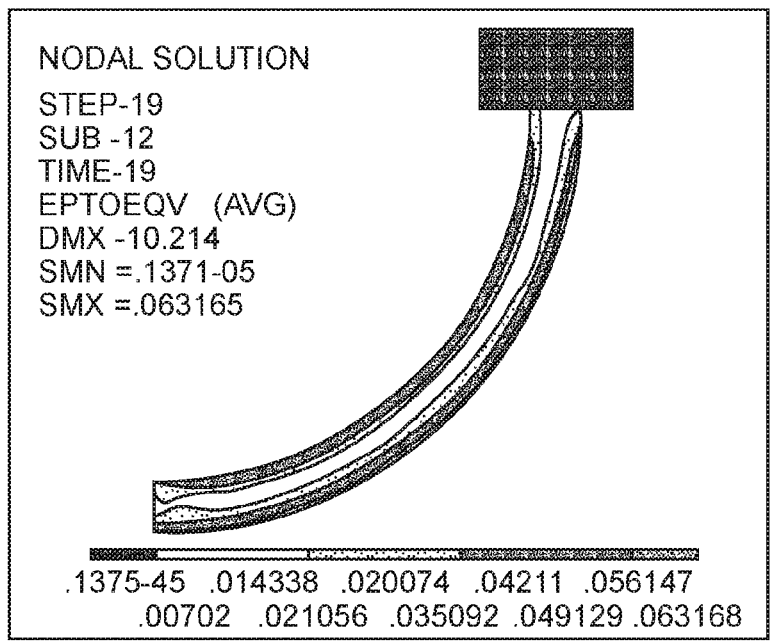
FIGS. 36 and 37 are plots of a finite element analysis showing the calculated stress of the portion of the tool member shown in FIG. 35 when deflected at an angle of 45 degrees.
Figure 37:
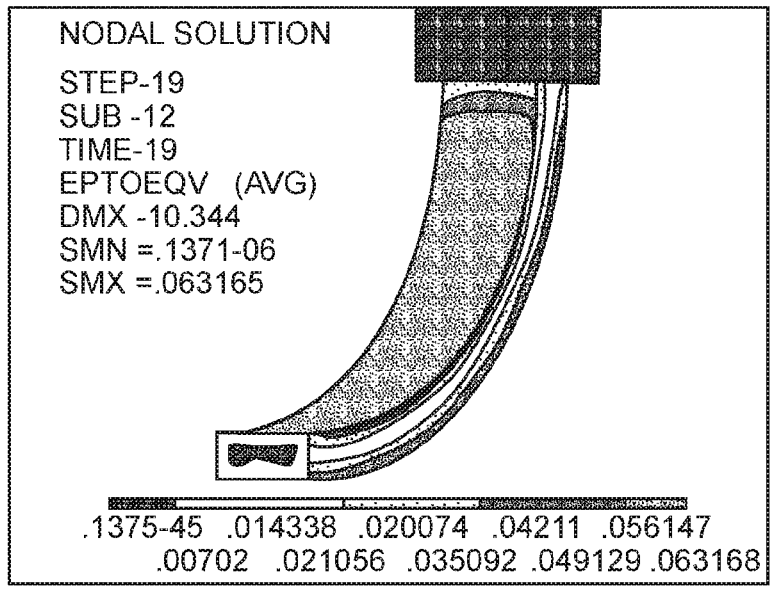

FIG. 35 is a schematic illustration of a portion of a flexure 671' of a compliant joint mechanism 600' that was used to model the flexure 671 of the actual compliant joint mechanism 600. The modeled flexure 671' is coupled to a base 610', and the moment arm was modeled such that it is rigid in comparison to the flexure. A follower force was applied to the end of the moment arm to deflect the flexure 671'. The mesh was refined in the flexure volume and approximately 30,000 elements were used. FIGS. 36 and 37 are plots of the finite element analysis showing the calculated stress of the flexure 671 (modeled as flexure 671'). As shown, the modeling predicts that the flexure 671 can undergo angular deflections over ~90 degrees before yielding occurs. Specifically, FIGS. 36 and 37 show the calculated stress of the flexure 671 (modeled as flexure 671') when deflected at an angle of about 88.6 degrees. At this deflection, the flexure has a total von Mises strain of 6.3%. For this strain level the flexure has an expected fatigue life of approximately 1000 cycles.

Figure 38:
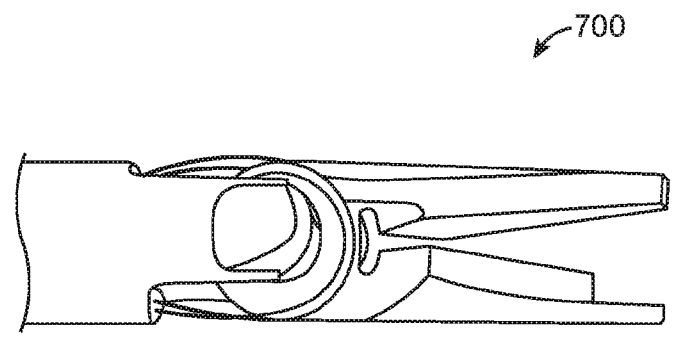
FIGS. 38 and 39 are photographs of a surgical assembly including a compliant joint mechanism, according to an embodiment.
Figure 39:
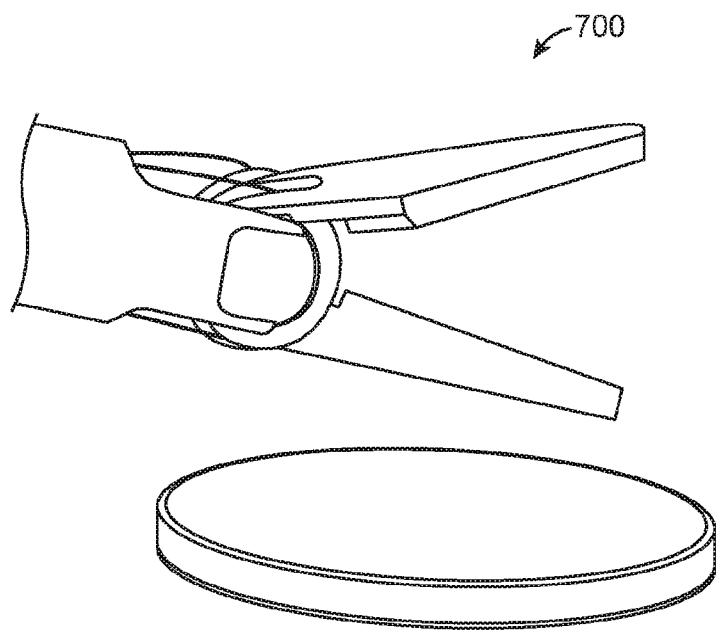

FIGS. 38 and 39 are photographs of a prototype compliant mechanism 700. The compliant mechanism 700 was fabricated based on the design of the compliant mechanism 600 shown and described above.

Although the tool member 620 is shown as including an actuation portion 632 having centrally-located, fully circular spool 630, and that defines a slot 634 through which the cables (e.g., cable 661) can be wrapped about the spool 638, in other embodiments a tool member can include any suitable spool design. For example, in some embodiments, a tool member can include any suitable spool (or pulley) design. For example, in some embodiments, a tool member can include a spool that is not fully circular (i.e., that is not a fully-enclosed circle). In some embodiments, for example, a spool can extend about 270 degrees about its center point, thus leaving the proximal portion open. In other embodiments, a spool can extend about 180 degrees about its center point.

Figure 40:
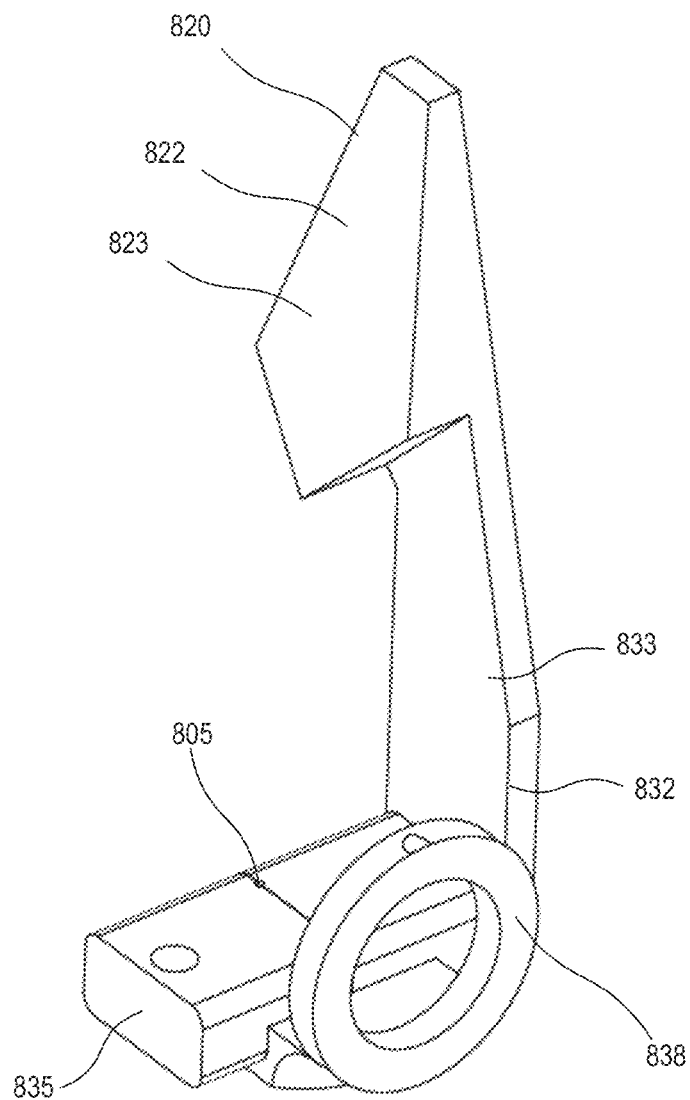
FIG. 40 is a perspective view of tool member for use in a compliant joint mechanism, according to an embodiment.

Moreover, in some embodiments, a tool member can include a spool or pulley that is offset from a central axis (also referred to as the axis of rotation) of the actuation portion. For example, FIG. 40 shows a perspective view of a tool member 820 that can be used in any of the compliant mechanisms, end effectors, or surgical instruments described herein. The tool member 820 includes an engagement portion 822 and an actuation portion 832. The engagement portion 822 is disposed distally from the actuation portion 832, and is configured to exert an engagement force (not shown, similar to the force $F_{OUT}$ shown in FIG. 4) on a target structure (not shown). Specifically, the engagement portion 822 includes an engagement surface 823.

The actuation portion 832 of the first tool member 820 is configured to receive actuation forces (similar to the forces $F_1$ and $F_2$ shown and described with reference to FIG. 28) to actuate the tool member 820. The actuation portion 832 includes a longitudinal portion (or arm) 833, a lateral portion (or arm) 835, and a spool 838 (also referred to as a pulley). The longitudinal arm 833 is substantially normal to the lateral arm 835. In contrast to the tool member 620 described above, the longitudinal arm 833 is devoid of any slot or "pass through" for cables. Instead, the spool 838 is offset from a centerline of the longitudinal arm 833. As shown, the lateral arm 835 defines two openings 805 that mount the flexure assembly (not shown) to the tool member 820.

Although the first flexure assembly 670 is shown as including two cylindrical flexures 871, in other embodiments, a flexure assembly or any of the flexures described herein can include any suitable flexure. For example, any of the flexures described herein can be constructed from any suitable material and can have any suitable geometric shape to provide the desired resilience, durability, and the like. For example, in some embodiments, a flexure can be a thin, planar strip of material. FIGS. 41-44 show a compliant joint mechanism 900 according to an embodiment. The joint mechanism 900 includes a shaft 902 having a ground member 910, a first tool member 920, a second tool member 940, and a first flexure 971, and a second flexure 972. The first tool member 920 and the second tool member 940 can be a portion of an end effector 904 for a surgical instrument, such as the instrument 500. The joint assembly 900 can be used in any suitable surgical device or system as described herein.

Figure 42:
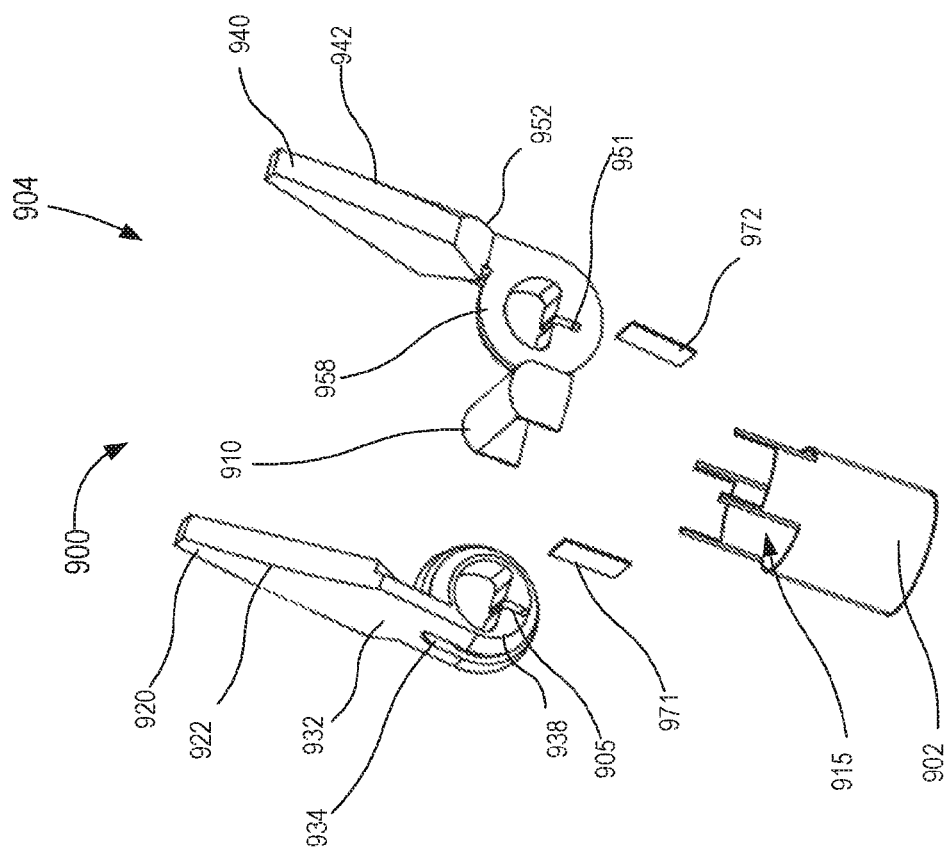
FIGS. 41 and 42 are a perspective view and an exploded view, respectively, of a surgical assembly including a compliant joint mechanism, according to an embodiment.
Figure 41:
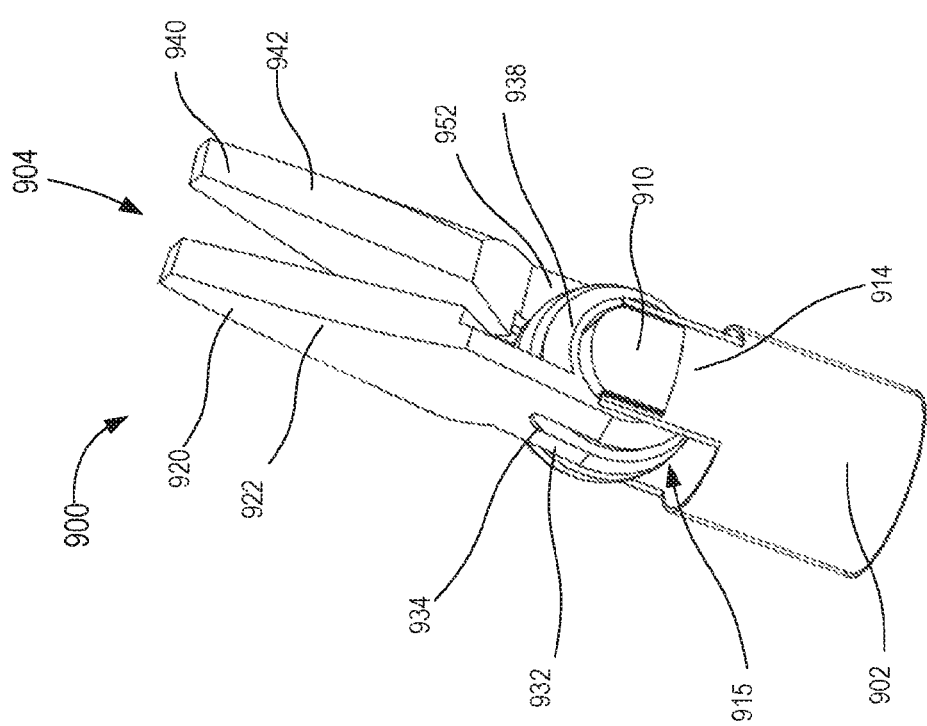
Figure 44:
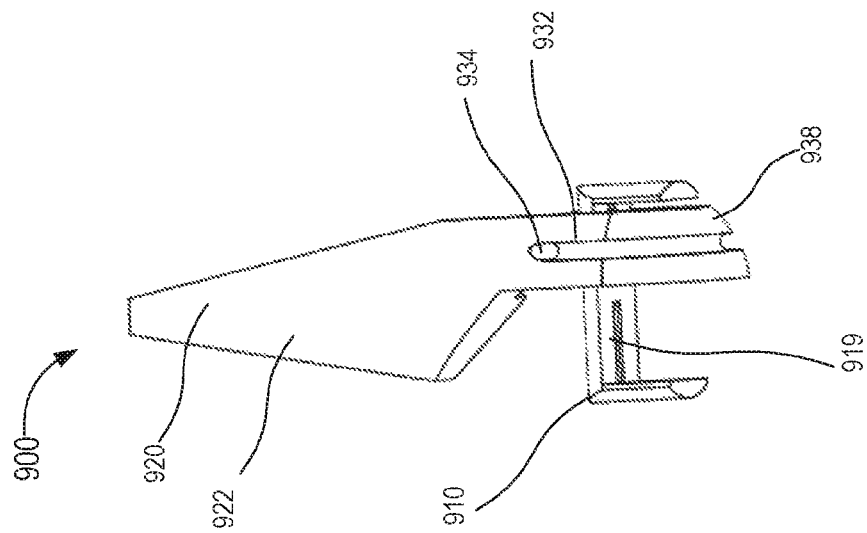
FIGS. 43 and 44 are perspective views of a portion of the surgical assembly shown in FIGS. 41 and 42.
Figure 43:
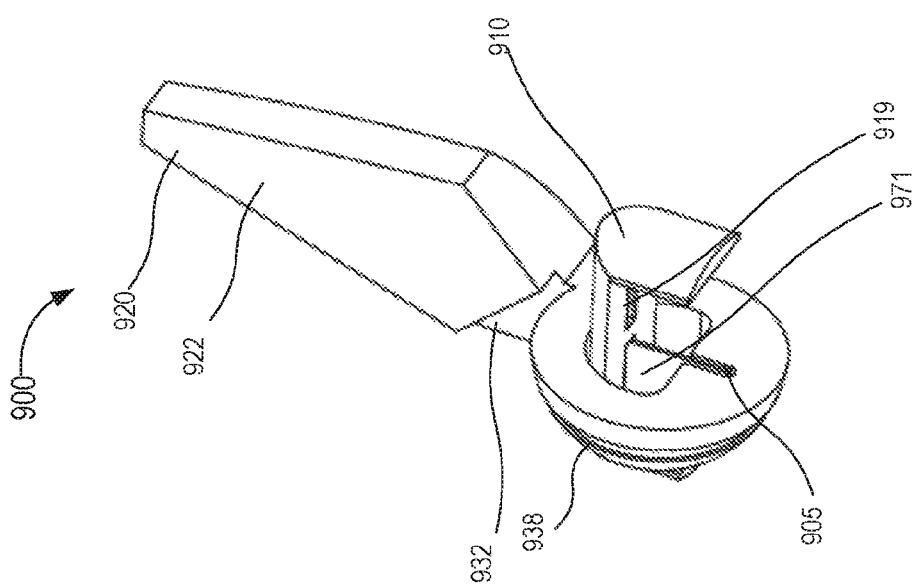

The shaft defines a longitudinal axis along which the distal and proximal directions are defined. The distal end portion of the shaft 902 defines an opening (slot) 915 that allows the tool members to rotate through the desired range of motion. The distal end portion of the shaft 902 also includes a mounting portion 914 to which the ground member 910 is fixedly coupled. As shown in FIG. 42, the mounting portion 914 defines a pair of slots that receive the ground member 910.

The ground member 910 is fixedly coupled to the shaft 902, and serves as a point of attachment for the first tool member 920 and the second tool member 940 (via the first flexure 971 and the second flexure 972, respectively). The ground member 910 includes a first end portion, a second end portion, and a central portion therebetween. Each of the first end portion and the second end portion are disposed within their respective mounting slot 906. The central portion 917 defines two openings 919 that receive the first flexure 971 and the second flexure 972. In the case shown, the openings 919 are in the form of slots.

The first tool member 920 includes an engagement portion 922 and an actuation portion 932. The engagement portion 922 is disposed distally from the actuation portion 932, and is configured to exert an engagement force (not shown, similar to the force $F_{OUT}$ shown in FIG. 4) on a target structure (not shown). The actuation portion 932 of the first tool member 920 is configured to receive the actuation forces (not shown, similar to the forces $F_1$ and $F_2$ in FIG. 28) to actuate the first tool member 920. The actuation portion 932 includes a spool 938 (also referred to as a pulley), and defines a slot 934 through which a cable (not shown) passes. In inner portion of the spool 938 defines an opening 905 within which the first flexure 971 is received to mount the first flexure 971 to the first tool member 920. In the case shown, the opening 905 is in the form of a slot.

The second tool member 940 includes an engagement portion 942 and an actuation portion 952. The engagement portion 942 is disposed distally from the actuation portion 952, and is configured to exert an engagement force (not shown, similar to the force $F_{OUT}$ shown in FIG. 4) on a target structure (not shown). The actuation portion 952 of the first tool member 940 is configured to receive the actuation forces (not shown, similar to the forces $F_1$ and $F_2$ in FIG. 28) to actuate the second tool member 940. The actuation portion 952 includes a spool 958 (also referred to as a pulley), and defines a slot 954 through which a cable (not shown) passes. In inner portion of the spool 958 defines an opening 951 within which the second flexure 972 is received to mount the second flexure 972 to the second tool member 940. In the case shown, the opening 951 is in the form of a slot.

The first tool member 920 and the second tool member 940 are coupled to the ground portion 910 via the first flexure 971 and the second flexure 972, respectively. Each of the first flexure 971 and the second flexure 972 have a first end portion that is coupled within a respective opening 919 defined by the ground member 910. Each of the first flexure 971 and the second flexure 972 have a second end portion that is coupled within a respective opening 905, 951. In this manner, the first tool member 920 and the second tool member 940 are each coupled to the shaft 902 in a manner that produces an inverted configuration, as described above.

Figure 45:
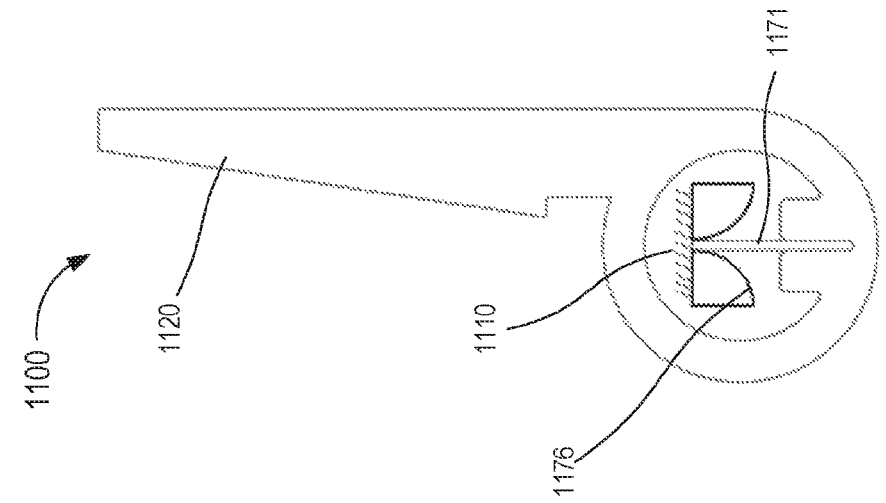
FIG. 45 is a side view of tool member for use in a compliant joint mechanism, according to an embodiment.

Although shown as being circular, in other embodiments, the spool 638 (or any other spool shown herein) can be any suitable shape. For example, in some embodiments, a spool can be elliptical shaped. For example, FIG. 45 shows a tool member 1020 having an elliptical shaped spool 1038. The joint mechanism also includes a thin, planar flexure 1071, similar to the flexure 971 described above.

Figure 46:
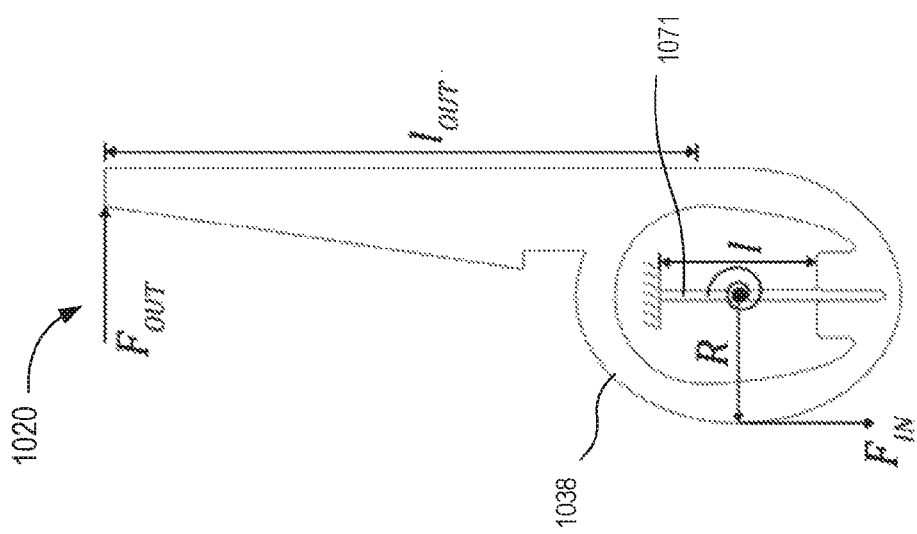
FIG. 46 is a side schematic illustration of tool member for use in a compliant joint mechanism, according to an embodiment.

In some embodiments, a joint assembly can include guide structures to guide the deflection of the flexures during use. For example, in some embodiments, a joint assembly can include guide structures on the shaft, ground portion, or any other suitable portion, that contact a portion of the flexure during use to guide the shape of deflection. For example, FIG. 46 shows a joint assembly 1100 that includes a tool member 1120 and a flexure 1171. The flexure is coupled to a ground member 1110, which also includes guide (or cam) surfaces 1176. The guide surfaces 1176 can constrain the radius of curvature of the flexure and therefore limit the stress to a predetermined value. This arrangement can increase the angular rotation of the mechanism for a given geometry. The guide surfaces 1176 may also constrain the flexure in a way that decreases the variation in the center of rotation of the mechanism, therefore decreasing misalignment of the jaws when they are deflected.

Figure 47:
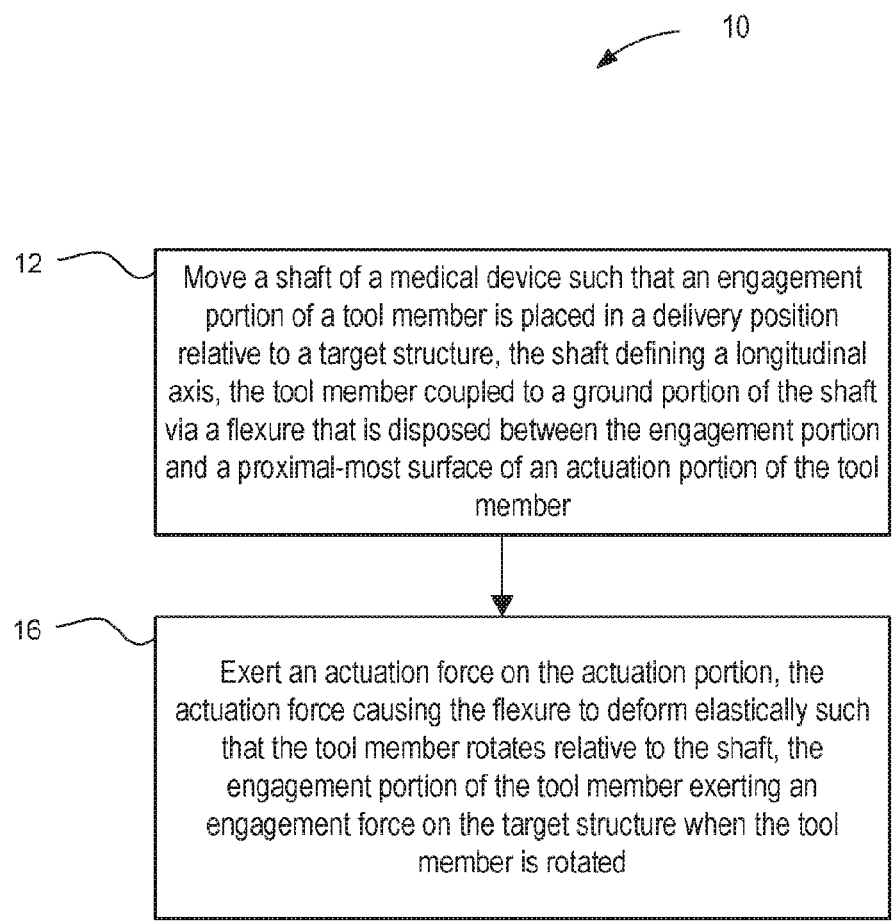
FIG. 47 is a flow diagram of a method of using a surgical assembly according to an embodiment.

FIG. 47 is a flow chart of a method 10 of manipulating an instrument, according to an embodiment. The method 10 can be performed using any of the devices, joint assemblies, or components thereof described herein. The method 10 includes moving a shaft of a medical device such that an engagement portion of a tool member is placed in a delivery position relative to a target structure, at 12. The shaft defines a longitudinal axis, and the tool member is coupled to a ground portion of the shaft via a flexure that is disposed between the engagement portion and a proximal-most surface of an actuation portion of the tool member. The method further includes exerting an actuation force on the actuation portion, at 16. The actuation force causes the flexure to deform elastically such that the tool member rotates relative to the shaft. In response, the engagement portion of the tool member exerts an engagement force on the target structure when the tool member is rotated.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the tool members can be constructed from any material, such as medical grade stainless steel, nickel alloys, titanium alloys or the like. Further, any of the tool members, such as the tool member 620, can be constructed from multiple pieces that are later joined together. For example, in some embodiments, a tool member can be constructed by joining together separately constructed components (e.g., the lateral arm, the spool, the longitudinal arm). In other embodiments, however, a tool member can be monolithically constructed. Similarly, in some embodiments a tool member can include an actuation portion, an engagement portion, and a spool that are monolithically constructed.

Although many of the joint mechanisms have been described herein as including a shaft having a ground portion (see, e.g., ground portion 110 and ground portion 310) or a ground member (see, e.g., ground member 610), in other embodiments, the ground portion or ground member of any of the joint mechanisms described herein can be coupled to any suitable portion of a medical device. For example, in some embodiments, a medical device can include a shaft, one or more wrist mechanisms, and one or more inverted joint mechanisms (of the types shown and described herein). In such embodiments, the ground portion (or member) of the inverted joint mechanism(s) can be coupled to a distal portion of a wrist mechanism, rather than being coupled directly to the shaft.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. An apparatus, comprising:
 a shaft comprising a distal end portion, a proximal end portion, and a longitudinal axis defined between the distal end portion and the proximal end portion, the distal end portion of the shaft comprising a ground portion;
 a tool member comprising an engagement portion and an actuation portion, the engagement portion being distal of the actuation portion along the longitudinal axis of the shaft, the engagement portion being configured to exert an engagement force on a target structure, the actuation portion being configured to receive an actuation force; and a flexure comprising a first end portion and a second end portion, the first end portion being coupled to the ground portion of the shaft, the second end portion being coupled to the tool member, the ground portion of the shaft being disposed distally of the flexure, the flexure being configured to deform elastically when the actuation force is exerted on the actuation portion of the tool member such that the tool member rotates relative to the shaft.

2. The apparatus of claim 1, wherein:
the actuation portion is coupled to an actuation cable that exerts the actuation force; and
a component of the actuation force has a proximal direction along the longitudinal axis.

3. The apparatus of claim 1, wherein:
the actuation portion of the tool member comprises a proximal-most surface; and
the flexure is between the engagement portion of the tool member and the proximal-most surface of the actuation portion of the tool member.

4. The apparatus of claim 1, wherein:
the actuation portion of the tool member comprises a proximal-most surface; and
the tool member is coupled to the shaft such that the ground portion of the shaft is between the engagement portion of the tool member and the proximal-most surface of the actuation portion of the tool member.

5. The apparatus of claim 1, wherein:
the actuation portion comprises a spool and an actuation cable routed around the spool;
the spool comprises a circular portion; and
the flexure is within the circular portion.

6. The apparatus of claim 5, wherein:
the flexure defines a pivot axis about which the tool member rotates when the actuation force is exerted on the actuation portion of the tool member;
a central axis of the circular portion is defined; and
the central axis is coaxial with the pivot axis.

7. The apparatus of claim 1, wherein:
the flexure defines a pivot axis about which the tool member rotates when the actuation force is exerted on the actuation portion of the tool member; and
the engagement portion of the tool member comprises an engagement surface defining an engagement plane that intersects the pivot axis.

8. The apparatus of claim 1, wherein:
the tool member is a first tool member, the engagement portion is a first engagement portion, the actuation force exerted on the actuation portion of the first tool member is a first actuation force, the engagement force exerted on the target structure is a first engagement force, and the flexure is a first flexure;
the apparatus further comprises a second tool member and a second flexure;
the second tool member comprises aft second engagement portion and a second actuation portion, the second engagement portion of the second tool member being configured to exert a second engagement force on the target structure between the first engagement portion of the first tool member and the second engagement portion of the second tool member, and the second actuation portion of the second tool member being configured to receive a second actuation force; and the second flexure comprises a first end portion coupled to the ground portion of the shaft and a second end portion coupled to the second tool member, the second flexure being configured to deform elastically when the second actuation force is exerted on the second actuation portion of the second tool member such that the second tool member rotates relative to the shaft.

9. The apparatus of claim 1, wherein:
the actuation portion is configured to receive the actuation force at an attachment point;
the tool member rotates relative to the shaft about a pivot axis when the actuation force is exerted on the actuation portion of the tool member; and
the actuation portion of the tool member is configured such that the attachment point is spaced apart from the pivot axis in a direction normal to the longitudinal axis by a moment distance, the moment distance varying by less than ten percent through an angular range of motion of the tool member.

10. The apparatus of claim 9, wherein:
the angular range of motion is at least ±45 degrees from the longitudinal axis.

11. The apparatus of claim 9, wherein:
the actuation portion of the tool member comprises a proximal-most surface; and
the tool member is coupled to the shaft such that the ground portion of the shaft is between the engagement portion of the tool member and the proximal-most surface of the actuation portion of the tool member.

12. The apparatus of claim 9, wherein:
the actuation portion comprises a spool for an actuation cable, and the spool comprises a circular portion;
the actuation force at the attachment point is tangent to the circular portion of the spool; and
the engagement portion, the actuation portion, and the spool are formed as a monolithic piece.

13. The apparatus of claim 12, wherein:
the spool has an axis of rotation; and
the axis of rotation is coaxial with the pivot axis.

14. The apparatus of claim 1, wherein:
the tool member is a first tool member, the actuation portion is a first actuation portion, the engagement portion is a first engagement portion, the actuation force exerted on the first actuation portion of the first tool member is a first actuation force, and the flexure is a first flexure;
the apparatus further comprises a second tool member and a second flexure;
the second tool member comprises a second engagement portion and a second actuation portion, the second actuation portion being configured to receive a second actuation force; and
the second flexure comprises a first end portion coupled to the ground portion of the shaft and a second end portion coupled to the second tool member, the second flexure being configured to deform elastically when the second actuation force is exerted on the second actuation portion of the second tool member such that the second tool member rotates relative to the shaft;
wherein the first actuation portion comprises a proximal-most surface, and the first flexure is between the proximal-most surface of the first actuation portion and the first engagement portion of the first tool member; and
the second actuation portion further comprises a proximal-most surface, and the second flexure is between the proximal-most surface of the second actuation portion and the second engagement portion of the second tool member.

15. The apparatus of claim 14, wherein:

the first tool member is configured to rotate relative to the second tool member such that the first engagement portion and the second engagement portion together exert the engagement force on the target structure between the first engagement portion and the second engagement portion.

16. The apparatus of claim 14, wherein:

the first engagement portion comprises a first engagement surface, and the first engagement surface defines a first plane;

the second engagement portion comprises a second engagement surface, and the second engagement surface defines a second plane;

the first engagement surface and the second engagement surface are configured to together exert the engagement force on the target structure between the first engagement portion and the second engagement portion;

the first tool member and the second tool member each rotate about a pivot axis; and the first plane and the second plane intersect the pivot axis.

17. The apparatus of claim 14, wherein:

the first engagement portion comprises a first engagement surface;

the second engagement portion comprises a second engagement surface;

the first engagement surface and the second engagement surface are configured to together exert the engagement force on the target structure between the first engagement portion and the second engagement portion; and an angle defined by the first engagement surface and the second engagement surface when the engagement force is exerted is less than five degrees through an angular range of motion of the first tool member and the second tool member.

18. The apparatus of claim 17, wherein:

the first tool member and the second tool member each have an angular range of motion of at least ±45 degrees from the longitudinal axis.

19. The apparatus of claim 14, wherein:

the ground portion of the shaft is between the first engagement portion and the proximal-most surface of the first actuation portion.

20. The apparatus of claim 14, wherein:

the first actuation portion comprises an attachment point, and the actuation force is received at the attachment point;

the first flexure defines a pivot axis in a direction normal to the longitudinal axis;

the first tool member moves through an angular range of motion about the pivot axis;

the first actuation portion is configured such that the attachment point is spaced apart from the pivot axis by a moment distance; and the moment distance varies by less than ten percent through the angular range of motion of the first tool member.

21. An apparatus, comprising:

a shaft comprising a distal end portion, a proximal end portion, and a longitudinal axis defined between the distal end portion and the proximal end portion, the distal end portion of the shaft comprising a ground portion;

a tool member comprising an engagement portion and an actuation portion, the engagement portion being distal of the actuation portion along the longitudinal axis of the shaft, the engagement portion being configured to exert an engagement force on a target structure, the actuation portion being configured to receive an actuation force; and a flexure comprising a distal end portion and a proximal end portion, the distal end portion of the flexure terminating at the ground portion of the shaft, the proximal end portion of the flexure being coupled to the tool member, the flexure being configured to deform elastically when the actuation force is exerted on the actuation portion of the tool member such that the tool member rotates relative to the shaft.

* * * * *

UNITED STATES PATENT AND TRADEMARK OFFICE
CERTIFICATE OF CORRECTION

PATENT NO. : 11,123,145 B2
APPLICATION NO. : 16/096985
DATED : September 21, 2021
INVENTOR(S) : Jason Dearden et al.

Page 1 of 1

It is certified that error appears in the above-identified patent and that said Letters Patent is hereby corrected as shown below:

In the Claims

Column 29, Line 59 (Claim 8): the phrase "tool member comprises aft second engagement" should be
-- tool member comprises a second engagement --

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*